United States Patent
Chung et al.

(10) Patent No.: US 10,392,353 B2
(45) Date of Patent: Aug. 27, 2019

(54) PROCESSES FOR MAKING SUBSTITUTED QUINAZOLINE COMPOUNDS USING HYDROGEN BONDING CATALYSTS

(71) Applicants: Merck Sharp & Dohme Corp., Rahway, NJ (US); Cheol K. Chung, Westfield, NJ (US); Guy R. Humphrey, Hillsborough, NJ (US); Zhijian Liu, Kendall Park, NJ (US); Mark McLaughlin, Summit, NJ (US); Yingju Xu, Edison, NJ (US); Younong Yu, East Brunswick, NJ (US)

(72) Inventors: Cheol K. Chung, Westfield, NJ (US); Guy R. Humphrey, Hillsborough, NJ (US); Zhijian Liu, Kendall Park, NJ (US); Mark McLaughlin, Summit, NJ (US); Yingju Xu, Edison, NJ (US); Younong Yu, East Brunswick, NJ (US)

(73) Assignee: Merck Sharp & Dohme Corp., Rahway, NJ (US)

(\*) Notice: Subject to any disclaimer, the term of this patent is extended or adjusted under 35 U.S.C. 154(b) by 0 days.

(21) Appl. No.: 15/778,505

(22) PCT Filed: Nov. 18, 2016

(86) PCT No.: PCT/US2016/062654
§ 371 (c)(1),
(2) Date: May 23, 2018

(87) PCT Pub. No.: WO2017/091453
PCT Pub. Date: Jun. 1, 2017

(65) Prior Publication Data
US 2018/0346429 A1     Dec. 6, 2018

Related U.S. Application Data

(60) Provisional application No. 62/259,167, filed on Nov. 24, 2015.

(51) Int. Cl.
*C07D 239/84*     (2006.01)
(52) U.S. Cl.
CPC ................... *C07D 239/84* (2013.01)

(58) Field of Classification Search
CPC .................................................. C07D 239/84
See application file for complete search history.

(56) References Cited

U.S. PATENT DOCUMENTS

| | | | |
|---|---|---|---|
| 7,196,086 B2 * | 3/2007 | Wunberg | C07D 239/84 514/252.17 |
| 2009/0221822 A1 | 9/2009 | Goossen et al. | |
| 2015/0045371 A1 | 2/2015 | Maertens et al. | |

FOREIGN PATENT DOCUMENTS

WO     2015088931 A1     6/2015

OTHER PUBLICATIONS

The International Search Report and Written Opinion for PCT/US2016/062654, dated Jan. 24, 2017, 9 pages.

\* cited by examiner

*Primary Examiner* — Emily A Bernhardt
(74) *Attorney, Agent, or Firm* — Jeffrey P. Bergman; Catherine D. Fitch

(57) ABSTRACT

Disclosed herein is a novel process for preparing substituted quinazoline compounds of formula (I) using a hydrogen bonding catalyst.

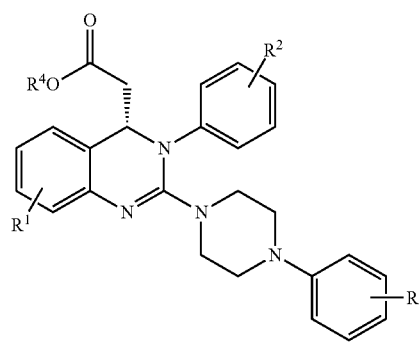

(I)

17 Claims, No Drawings

PROCESSES FOR MAKING SUBSTITUTED QUINAZOLINE COMPOUNDS USING HYDROGEN BONDING CATALYSTS

CROSS-REFERENCE TO RELATED APPLICATIONS

This application is the national stage application under 35 U.S.C. 371 of International Patent Application No. PCT/US2016/062654, filed Nov. 18, 2016, which claims priority to U.S. Provisional Patent Application No. 62/259,167, filed Nov. 24, 2015. Each of the aforementioned applications is incorporated by reference in its entirety.

FIELD OF THE INVENTION

The present invention is directed to novel processes for making substituted quinazoline compounds which are useful for the treatment or prophylaxis of HCMV infection.

BACKGROUND OF THE INVENTION

Human cytomegalovirus (HCMV) is ubiquitously distributed in the human population. In immunocompetent adults infections are mainly asymptomatic, but in immunocompromised patients, such as transplant recipients or AIDS patients, life threatening infections occur at a high rate. HCMV is also the leading cause of birth defects among congenitally transmitted viral infections.

Various substituted heterocyclic compounds are inhibitors of the HCMV terminase enzyme. Included in these heterocycles are quinazolines related to Compound A, as defined and described below. These compounds and pharmaceutically acceptable salts thereof are useful in the treatment or prophylaxis of infection by HCMV and in the treatment, prophylaxis, or delay in the onset or progression of HCMV infection. Representative quinazoline compounds that are useful for treating HCMV infection are described, for example, in U.S. Pat. No. 7,196,086. Among the compounds disclosed in U.S. Pat. No. 7,196,086, is (S)-2-(8-fluoro-3-(2-methoxy-5-(trifluoromethyl)phenyl)-2-(4-(3-methoxyphenyl)piperazin-1-yl)-3,4-dihydroquinazolin-4-yl)acetic acid, hereinafter referred to as Compound A. Compound A is a known inhibitor of HCMV terminase. The structure of Compound A is as follows:

Compound A

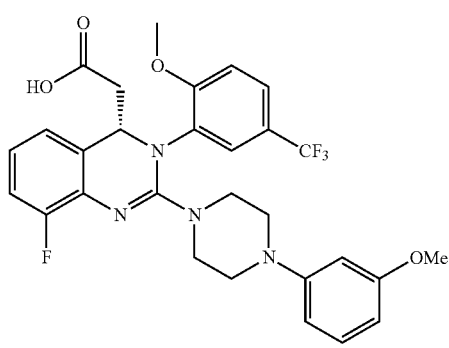

U.S. Pat. Nos. 7,196,086 and 8,084,604 and PCT Publication No. WO2015/088931 disclose methodology and synthetic routes that can be used to prepare Compound A and related quinazoline-based HCMV terminase inhibitors. However, the currently known methods have various drawbacks and there remains a need for improved synthetic methods for preparing Compound A and related compounds.

SUMMARY OF THE INVENTION

Disclosed herein are novel processes for making substituted quinazoline compounds of Formula (I) which are useful for the treatment and prophylaxis of HCMV infection. Specifically, these processes use various hydrogen bonding catalysts disclosed herein for the preparation of compounds of Formula I:

(I)

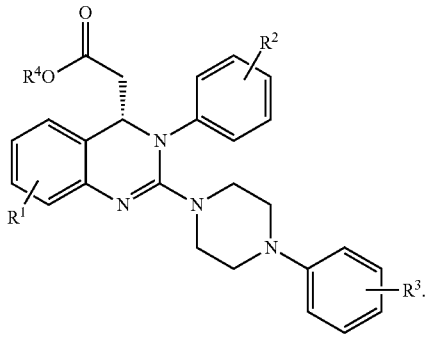

In one embodiment, a process for preparing a compound of formula (I) comprises contacting a compound of formula (viii):

(viii)

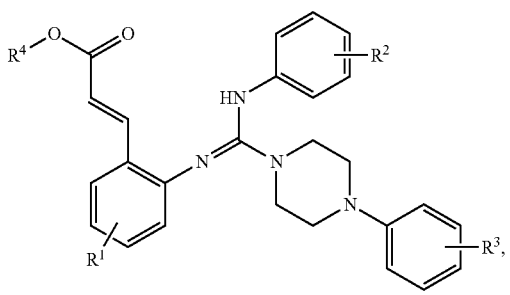

or a salt thereof, with a hydrogen bonding catalyst in a suitable solvent for a time sufficient to form a compound of formula (I), wherein:

$R^1$ represents up to 3 phenyl group substituents, each independently selected from $C_1$-$C_6$ alkyl, $C_1$-$C_6$ haloalkyl, halo, —CN, —OH and $C_1$-$C_6$ alkoxy;

$R^2$ represents up to 3 phenyl group substituents, each independently selected from $C_1$-$C_6$ alkyl, $C_1$-$C_6$ haloalkyl, halo, —CN, —OH and $C_1$-$C_6$ alkoxy;

$R^3$ represents up to 3 phenyl group substituents, each independently selected from $C_1$-$C_6$ alkyl, $C_1$-$C_6$ haloalkyl, halo, —CN, —OH and $C_1$-$C_6$ alkoxy; and $R^4$ is $C_1$-$C_6$ alkyl or $C_3$-$C_7$ cycloalkyl.

DETAILED DESCRIPTION OF THE INVENTION

Disclosed herein are processes using novel hydrogen bonding catalysts for making substituted quinazoline compounds of Formula (I) which are useful for inhibiting the replication of HCMV and for the treatment or prophylaxis of HCMV infection.

In one embodiment, a process for preparing a compound of formula (I):

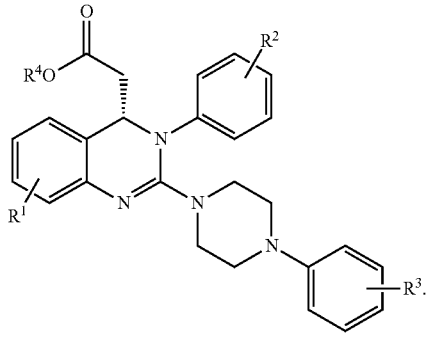

(I)

comprises contacting a compound of formula (viii):

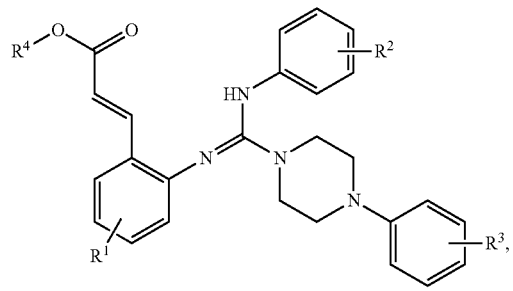

(viii)

or a salt thereof, with a hydrogen bonding catalyst in a suitable solvent for a time sufficient to form a compound of formula (I), wherein:

$R^1$ represents up to 3 phenyl group substituents, each independently selected from $C_1$-$C_6$ alkyl, $C_1$-$C_6$ haloalkyl, halo, —CN, —OH and $C_1$-$C_6$ alkoxy;

$R^2$ represents up to 3 phenyl group substituents, each independently selected from $C_1$-$C_6$ alkyl, $C_1$-$C_6$ haloalkyl, halo, —CN, —OH and $C_1$-$C_6$ alkoxy;

$R^3$ represents up to 3 phenyl group substituents, each independently selected from $C_1$-$C_6$ alkyl, $C_1$-$C_6$ haloalkyl, halo, —CN, —OH and $C_1$-$C_6$ alkoxy; and $R^4$ is $C_1$-$C_6$ alkyl or $C_3$-$C_7$ cycloalkyl.

The use of the instant hydrogen bonding catalysts is novel for this type of transformation and the instant processes are more simplified compared to known processes. In one embodiment, the instant processes have the unexpected advantage of producing compounds of formula (I) with higher enantiomeric excess (ee). Enantiomeric excess is a measurement of purity used for chiral substances. It reflects the degree to which a sample contains one enantiomer in greater amounts than the other. For example, a racemic mixture has an ee of 0%, while a single completely pure enantiomer has an ee of 100%. A sample with 70% of one enantiomer and 30% of the other has an ee of 40%.

In one embodiment, the instant processes have the unexpected advantage of producing compounds of formula (I) with higher yields.

In one embodiment, the hydrogen bonding catalyst is a bis-triflate compound of formula (V):

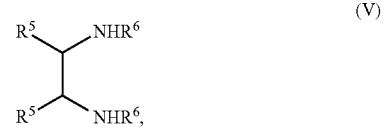

(V)

each occurrence of $R^5$ is independently selected from the group consisting of optionally substituted aryl, optionally substituted heteroaryl, and $C_1$-$C_6$alkyl optionally substituted with one to four halogens; and each occurrence of $R^6$ is independently selected from the group consisting of —$SO_2$—$C_1$-$C_6$alkyl optionally substituted with one to nine halogens, —$SO_2$-aryl, —$SO_2$-heteroaryl, and nonaflate ("Nf").

In one embodiment, each occurrence of $R^5$ is independently selected from the group consisting of phenyl, naphthyl and pyridine; wherein each of the phenyl and naphthyl is optionally substituted with one to three substituents independently selected from halogen, —O—$C_1$-$C_4$alkyl, —CN, sulfonate, —$NO_2$, phosphonate, $C_1$-$C_4$alkyl optionally substituted with one to four halogens, —O-Tf, and —O-Ts-$CF_3$.

In one embodiment, each occurrence of $R^6$ is independently selected from the group consisting of triflate ("Tf") and nonaflate ("Nf"). In one embodiment, each occurrence of $R^6$ is Tf. In one embodiment, each occurrence of $R^6$ is Nf.

In one embodiment, the catalyst of formula (V) is a compound of formula (Va):

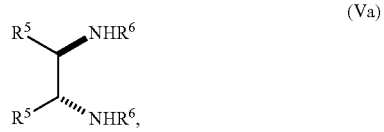

(Va)

wherein substituents $R^5$ and $R^6$ are as defined above for formula (V).

In one embodiment, the catalyst of formula (V) or (Va) is a compound selected from the group consisting of:

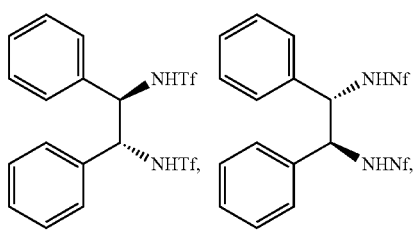

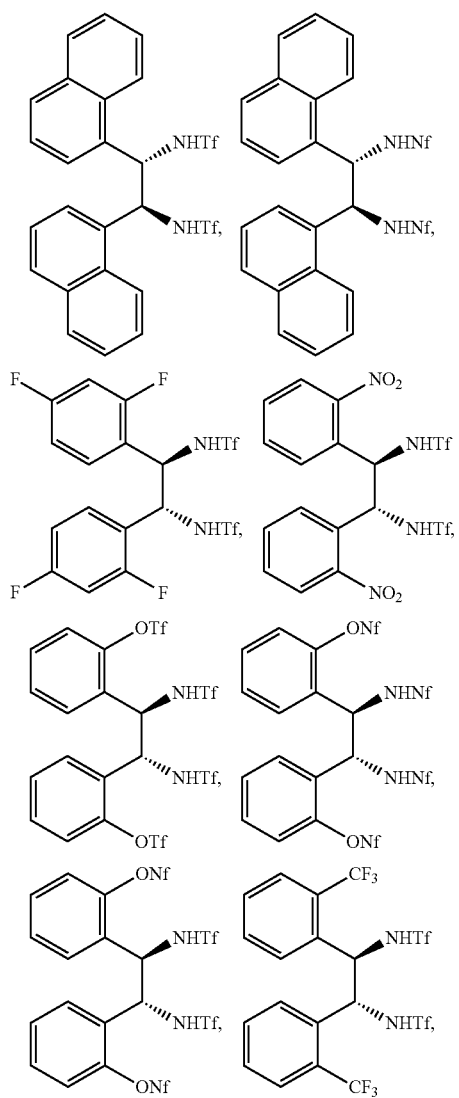

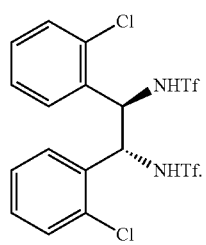

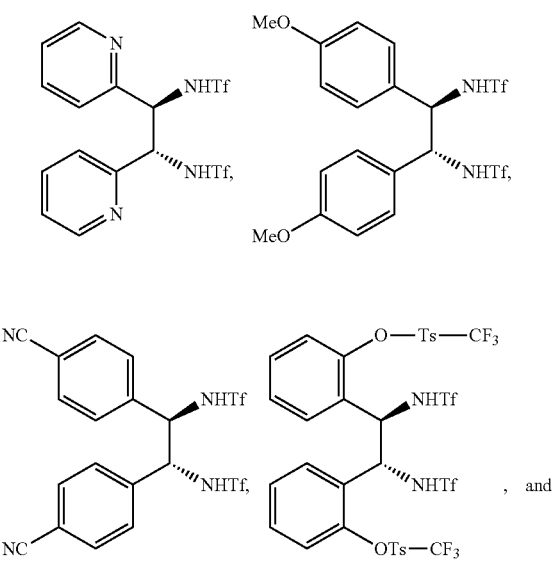

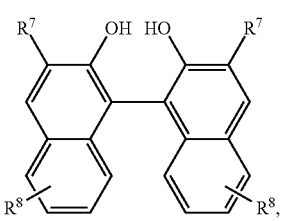

In one embodiment, a hydrogen bonding catalyst is a compound of formula (VI):

$$\text{(VI)}$$

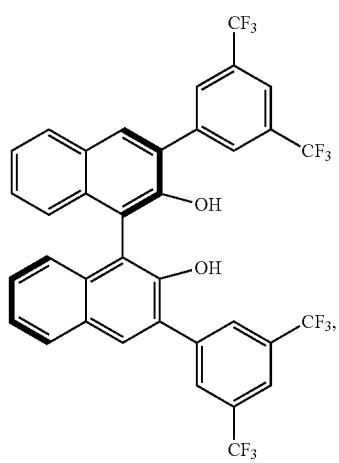

wherein each occurrence of R is independently selected from the group consisting of halogen, $C_1$-$C_6$alkyl optionally substituted with one to four halogens, $C_1$-$C_6$alkoxy, optionally substituted aryl, and optionally substituted heteroaryl; and each occurrence of $R^8$ is independently selected from the group consisting of hydrogen, halogen, $C_1$-$C_6$alkyl, $C_1$-$C_6$alkoxy, halo-$C_1$-$C_6$alkyl, optionally substituted aryl, and optionally substituted heteroaryl.

In one embodiment, each occurrence of $R^7$ is independently selected from the group consisting of phenyl, naphthyl, phenanthrenyl, pyridyl and thiophenyl, each of which is optionally substituted with one to five substituents independently selected from halogen and —$CF_3$.

In one embodiment, each occurrence of $R^8$ is hydrogen.

In one embodiment, the catalyst of formula (VI) is a compound selected from the group consisting of:

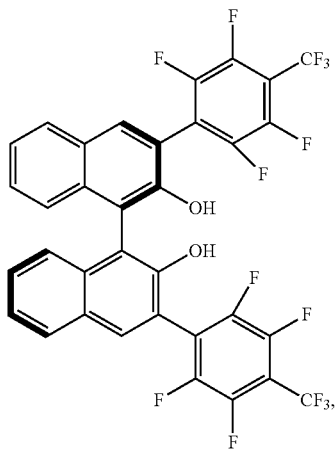
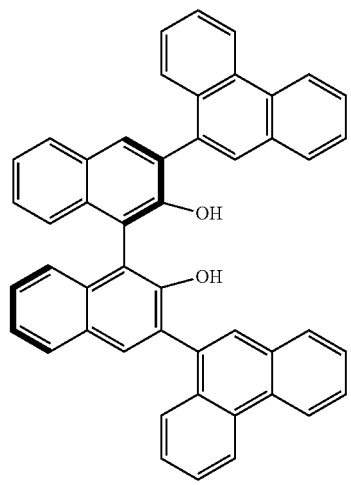
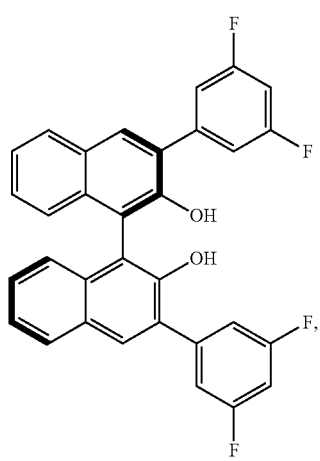
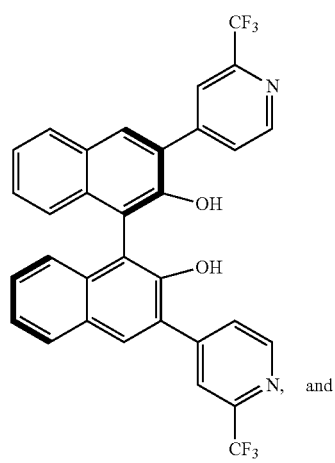
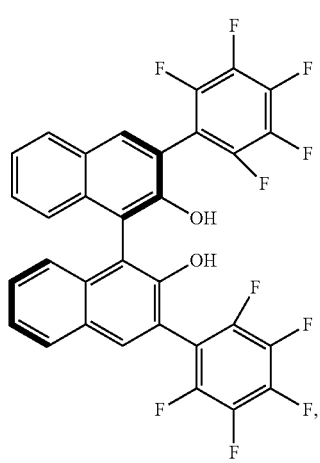
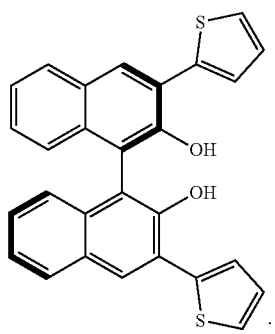
and
In one embodiment, a suitable solvent for a bis-triflate or binol catalyzed reaction to obtain a compound of formula (I) is selected from the group consisting of acetone, toluene, CF$_3$-toluene, dichloromethane, DCE, THF, chlorobenzene, 1,2-dichlorobenzene, MTBE, cyclopentyl methyl ether (CPME), acetonitrile, EtOAc, IPAc, MeOAc, nitromethane, trifluoromethylbenzene, methyl ethyl ketone, DME, anisole, hexafluorobenzene, o-xylene, fluorobenzene, 1,4-dioxane, iPr$_2$O and 2-MeTHF.

In one embodiment, the solvent used for a bis-triflate catalyzed reaction is toluene, MTBE or CPME.

In one embodiment, the solvent used for a binol catalyzed reaction is CF$_3$-toluene, chlorobenzene or 1,2-dichlorobenzene.

In one embodiment, a reaction to obtain a compound of formula (I) is carried out at a temperature of from about 5° C. to about 80° C. when a catalyst of formula (V) or (Va) is used. In another embodiment, the temperature is in a range from about 10° C. to about 70° C. In another embodiment, the temperature is in a range from about 20° C. to about 60° C. In another embodiment, the temperature is in a range from about 25° C. to about 50° C.

In one embodiment, a reaction to obtain a compound of formula (I) is carried out at a temperature in a range from about 30° C. to about 100° C. when a catalyst of formula (VI) is used. In another embodiment, the temperature is in a range from about 40° C. to about 90° C.

In another embodiment, the temperature is in a range from about 50° C. to about 80° C. In another embodiment, the temperature is in a range from about 50° C. to about 70° C. In another embodiment, the temperature is about 55° C. to about 65° C.

In one embodiment, the catalysts disclosed herein are more stable compared to known catalysts for this type transformation. In another embodiment, these catalysts are recyclable and more environmentally friendly.

In one embodiment, the compound of formula (I) that is made by the above processes is the compound of formula (III):

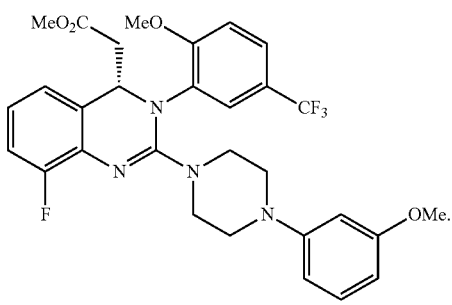

(III)

The starting material, a compound of formula (viii), can be readily prepared, for example, as described in PCT Application No. PCT/US14/068981 published as WO2015/088931.

Other embodiments, aspects and features of the present invention are either further described in or will be apparent from the ensuing description, examples, and appended claims.

Definitions and Abbreviations

The term "alkyl" as used herein, refers to an aliphatic hydrocarbon group, having from 1 to 20 carbon atoms wherein one of its hydrogen atoms is replaced with a bond. An alkyl group may be straight or branched. In one embodiment, an alkyl group has from 1-6 carbon atoms ("C$_1$-C$_6$alkyl"). In another embodiment, an alkyl group has from 1-4 carbon atoms ("C$_1$-C$_4$alkyl"). Non-limiting examples of C$_1$-C$_6$ alkyl groups include methyl, ethyl, n-propyl, isopropyl, n-butyl, sec-butyl, isobutyl, tert-butyl, n-pentyl, neopentyl, isopentyl, n-hexyl, isohexyl and neohexyl. Non-limiting examples of C$_1$-C$_4$ alkyl groups include methyl, ethyl, n-propyl, isopropyl, n-butyl, sec-butyl, isobutyl and tert-butyl. An alkyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)— cycloalkyl, —C(O)OH and —C(O)O-alkyl. In one embodiment, a C$_1$-C$_6$ alkyl group is linear. In another embodiment, a C$_1$-C$_6$ alkyl group is branched. Unless otherwise indicated, a C$_1$-C$_6$ alkyl group is unsubstituted.

The term "alkenyl," as used herein, refers to an aliphatic hydrocarbon group containing at least one carbon-carbon double bond and having one of its hydrogen atoms replaced with a bond. An alkenyl group may be straight or branched and contain from about 2 to about 15 carbon atoms. In one embodiment, an alkenyl group contains from about 2 to about 12 carbon atoms. In another embodiment, an alkenyl group contains from about 2 to about 6 carbon atoms ("C$_2$-C$_6$ alkenyl"). Non-limiting examples of alkenyl groups include ethenyl, propenyl, n-butenyl, 3-methylbut-2-enyl, n-pentenyl, octenyl and decenyl. An alkenyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O-alkyl. The term "C$_2$-C$_6$ alkenyl" refers to an alkenyl group having from 2 to 6 carbon atoms. Unless otherwise indicated, an alkenyl group is unsubstituted.

The term "alkynyl," as used herein, refers to an aliphatic hydrocarbon group containing at least one carbon-carbon triple bond and having one of its hydrogen atoms replaced with a bond. An alkynyl group may be straight or branched and contain from about 2 to about 15 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl. An alkynyl group may be unsubstituted or substituted by one or more substituents which may be the same or different, each substituent being independently selected from the group consisting of halo, alkenyl, alkynyl, aryl, cycloalkyl, cyano, hydroxy, —O-alkyl, —O-aryl, -alkylene-O-alkyl, alkylthio, —NH$_2$, —NH(alkyl), —N(alkyl)$_2$, —NH(cycloalkyl), —O—C(O)-alkyl, —O—C(O)-aryl, —O—C(O)-cycloalkyl, —C(O)OH and —C(O)O— alkyl. The term "C$_2$-C$_6$ alkynyl" refers to an alkynyl group having from 2 to 6 carbon atoms. Unless otherwise indicated, an alkynyl group is unsubstituted.

The term "$C_1$-$C_6$ hydroxyalkyl" as used herein, refers to $C_1$-$C_6$ alkyl group, as defined above, wherein one of the $C_1$-$C_6$ alkyl group's hydrogen atoms is replaced with a —OH group. A $C_1$-$C_6$ hydroxyalkyl group may be straight or branched and contain. Non-limiting examples of $C_1$-$C_6$ hydroxyalkyl groups include methanol, ethanol, isopropanol, and tert-butanol.

The term "aryl" refers to phenyl, naphthyl or phenanthrenyl. In one embodiment, an aryl group is phenyl. In one embodiment, an aryl group is naphthyl. In one embodiment, an aryl group is phenanthrenyl.

The term "3 to 7-membered cycloalkyl" refers to a refers to a non-aromatic mono- or ring system comprising from about 3 to about 7 ring carbon atoms. Examples of "3 to 7-membered cycloalkyls include cyclopropyl, cyclobutyl, cyclopentyl, cyclohexyl and cycloheptyl. A 3 to 7-membered cycloalkyl group can be optionally substituted with one or more "ring system substituents" which may be the same or different, and are as defined herein below. In one embodiment, a 3 to 7-membered cycloalkyl group is unsubstituted. A ring carbon atom of a 3 to 7-membered cycloalkyl may be functionalized as a carbonyl group. An illustrative example of such a 3 to 7-membered cycloalkyl (also referred to herein as a "cycloalkanoyl" group) includes, but is not limited to, cyclobutanoyl:

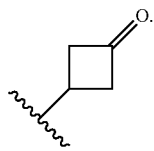 [SMILES: *C1CC(=O)C1]

The term "halo" or "halogen" as used herein, refers to fluorine, chlorine, bromine and iodine (alternatively referred to as fluoro, chloro, bromo, and iodo).

The term "5 or 6-membered monocyclic heteroaryl," as used herein, refers to an aromatic monocyclic ring system comprising about 5 to about 6 ring atoms, wherein from 1 to 4 of the ring atoms is independently O, N or S and the remaining ring atoms are carbon atoms. A 5 or 6-membered monocyclic heteroaryl group can be optionally substituted by one or more "ring system substituents" which may be the same or different, and are as defined herein below. A 5 or 6-membered monocyclic heteroaryl group is joined via a ring carbon atom, and any nitrogen atom of a heteroaryl can be optionally oxidized to the corresponding N-oxide. The term "5 or 6-membered monocyclic heteroaryl" also encompasses a 5 or 6-membered monocyclic heteroaryl group, as defined above, which is fused to a benzene ring. Non-limiting examples of 5 or 6-membered monocyclic heteroaryls include pyridyl, pyrazinyl, furanyl, thienyl, pyrimidinyl, pyridone (including N-substituted pyridones), isoxazolyl, isothiazolyl, oxazolyl, oxadiazolyl, thiazolyl, pyrazolyl, furazanyl, pyrrolyl, triazolyl, 1,2,4-thiadiazolyl, pyrazinyl, pyridazinyl, benzofurazanyl, indolyl, azaindolyl, benzimidazolyl, benzothienyl, imidazolyl, benzimidazolyl, thienopyridyl, thienopyrimidyl, pyrrolopyridyl, imidazopyridyl, isoquinolinyl, 1,2,4-triazinyl, benzothiazolyl and the like, and all isomeric forms thereof. Unless otherwise indicated, a 5 or 6-membered monocyclic heteroaryl group is unsubstituted.

The term "9 or 10-membered bicyclic heteroaryl," as used herein, refers to an aromatic bicyclic ring system comprising about 9 to about 10 ring atoms, wherein from 1 to 4 of the ring atoms is independently O, N or S and the remaining ring atoms are carbon atoms. A 9 or 10-membered bicyclic heteroaryl group can be optionally substituted by one or more "ring system substituents" which may be the same or different, and are as defined herein below. A 9 or 10-membered bicyclic heteroaryl group is joined via a ring carbon atom, and any nitrogen atom of a heteroaryl can be optionally oxidized to the corresponding N-oxide. Non-limiting examples of 9 or 10-membered bicyclic heteroaryls include and the like, and all isomeric forms thereof. Unless otherwise indicated, a 9 or 10-membered bicyclic heteroaryl group is unsubstituted.

Unless expressly stated to the contrary in a particular context, any of the various cyclic rings and ring systems described herein may be attached to the rest of the compound of which they are a part at any ring atom (i.e., any carbon atom or any heteroatom) provided that a stable compound results.

Unless expressly stated to the contrary, all ranges cited herein are inclusive; i.e., the range includes the values for the upper and lower limits of the range as well as all values in between.

When any variable occurs more than one time in a compound involved in the process of the invention (e.g., $R^f$), its definition on each occurrence is independent of its definition at every other occurrence. Also, combinations of substituents and/or variables are permissible only if such combinations result in a stable compound.

Unless expressly stated to the contrary, substitution by a named substituent is permitted on any atom in a ring (e.g., cycloalkyl, aryl, or heteroaryl) provided such ring substitution is chemically allowed and results in a stable compound.

In reference to the compounds employed as reactants or reagents in the process of the invention, a "stable" compound is one whose structure and properties remain or can be caused to remain essentially unchanged for a period of time sufficient to allow its use in the process of the invention so as to achieve the preparation of Compound of Formula (I). In reference to Compound of Formula (I), a "stable" compound is a compound which can be prepared in accordance with the process of the present invention and then isolated and whose structure and properties remain or can be caused to remain essentially unchanged for a period of time sufficient to allow use of the compound for its intended purpose; e.g., for the therapeutic administration to a subject who has HCMV infection.

The following abbreviations are used below and have the following meanings: Ac is acetyl; t-Bu is tertiary butyl; DCB is 1,2-dichlorobenzene; DCE is 1,2-dichloroethane; DCM is dichloromethane; DMAP is N,N-dimethylaminopyridine; DME is dimethoxyethane; DTTA is di-P-toluoyl-D-tartaric acid; EA is ethyl acetate; Et is ethyl; HPLC is high performance liquid chromatography; IPAC is isopropyl acetate; i-Pr is isopropyl; LC/MS is liquid chromatography/Mass Spectrometry; Me is methyl; MTBE is methyl tert-butyl ether; Ph is phenyl; pin is pinacol; THF is tetrahydrofuran; TLC is thin-layer chromatography and Ts is p-toluenesulfonate.

EXPERIMENTAL

In one embodiment, reactions were carried out with the bis-triflate catalyst as shown below at about 50° C. using different solvents shown in the following table. The conversion rate (%) and % e.e. for each reaction is included in the table.

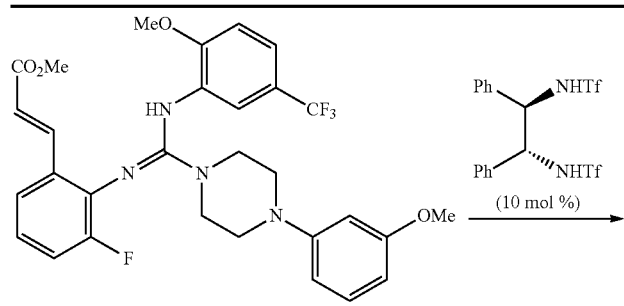

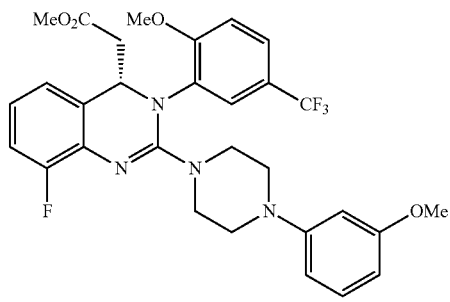 [SMILES: COC(=O)C[C@H]1c2cccc(F)c2N=C(N2CCN(c3cccc(OC)c3)CC2)N1c1cc(C(F)(F)F)ccc1OC]

| Solvent | Conversion | e.e. (%) | Solvent | Conversion | e.e. (%) |
| --- | --- | --- | --- | --- | --- |
| hexafluorobenzene | 100% | 51% | MTBE | 100% | 86% |
| octafluorotoluene | 100% | 72% | 2-MeTHF | 95% | 85% |
| toluene | 100% | 83% | THF | 53% | 84% |
| o-xylene | 100% | 82% | DME | 99% | 87% |
| F—Ph | 100% | 83% | EtOAc | 88% | 87% |
| Cl—Ph | 100% | 82% | IPAC | 88% | 87% |
| 1,2-DCB | 100% | 80% | DCE | 100% | 81% |
| CF3—Ph | 100% | 79% | acetone | 99% | 80% |
| 1,4-dioxane | 58% | 85% | cyclopentanone | 89% | 51% |
| iPr2O | 60% | 70% | cyclohexanone | 100% | 26% |
| anisole | 100% | 86% | PhCN | 100% | 79% |
| CPME | 100% | 85% | MeCN | 100% | 69% |

In one embodiment, reactions were carried out with the binol catalyst as shown below at about 60° C. using different solvents shown in the following table. The conversion rate (%) and % e.e. for each reaction is included in the table.

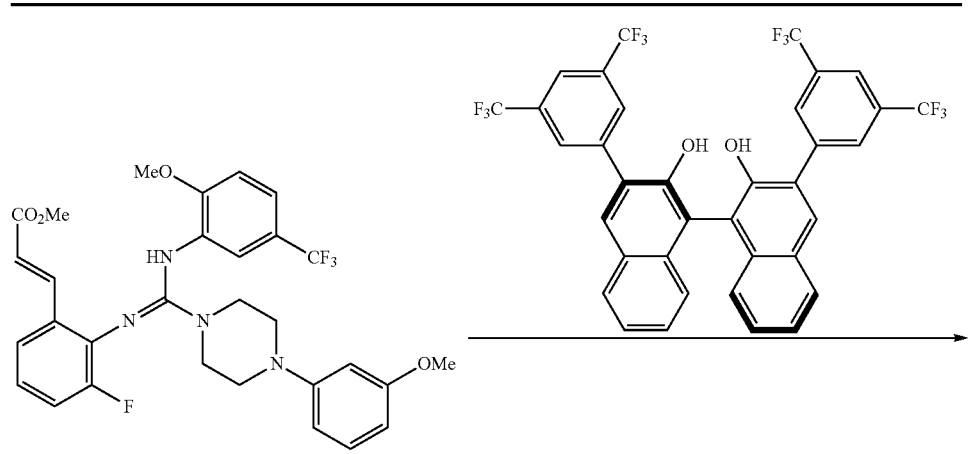

-continued

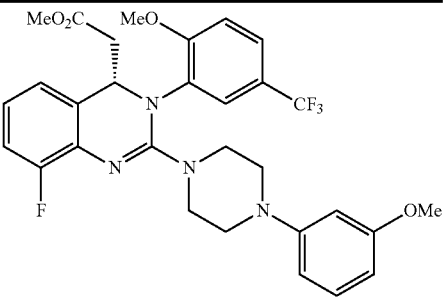

| Solvent | Conversion | e.e. (%) |
|---|---|---|
| Toluene | 70% | 70% |
| $C_6F_6$ | 98% | 68% |
| CPME | 34% | 35% |
| Anisole | 51% | 55% |
| Cl—Ph | 79% | 72% |
| F—Ph | 83% | 70% |
| 2MeTHF | 12% | 27% |
| IPAC | 28% | 24% |
| DME | 25% | 4% |
| 1,2-$Cl_2$—Ph | 88% | 75% |
| $CF_3$—Ph | 99% | 76% |
| Ph-CN | 70% | 17% |

In one embodiment, each reaction was carried out with a different catalyst shown in the following table at about 35° C. to about 50° C. Solvents used and the corresponding % e.e.'s are included in the table.

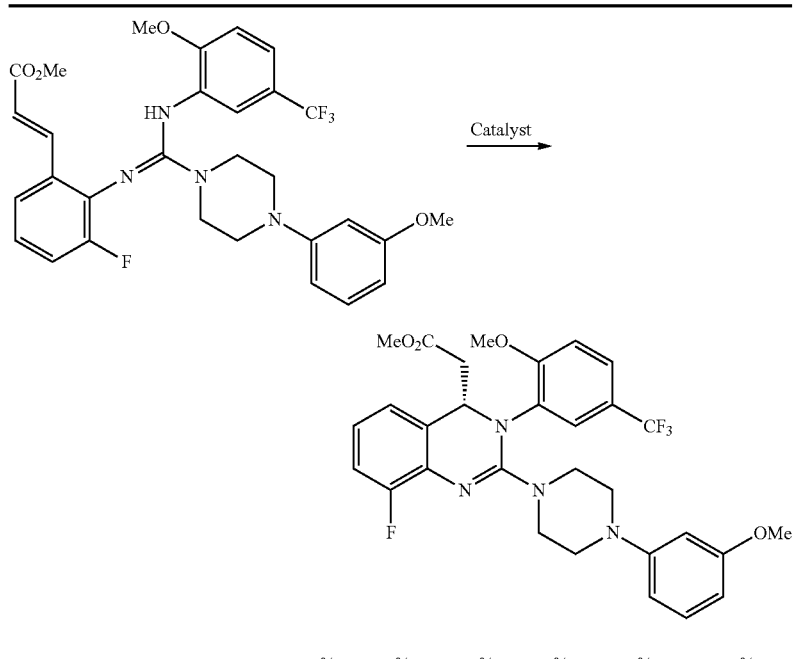

| Catalyst | ee % (EA) | ee % (Toluene) | ee % (CPME) | ee % (MTBE) | ee % (Anisole) | ee % (2-MeTHF) |
|---|---|---|---|---|---|---|
|  | 88 | 83 | 85 | 86 | 86 | 85 |

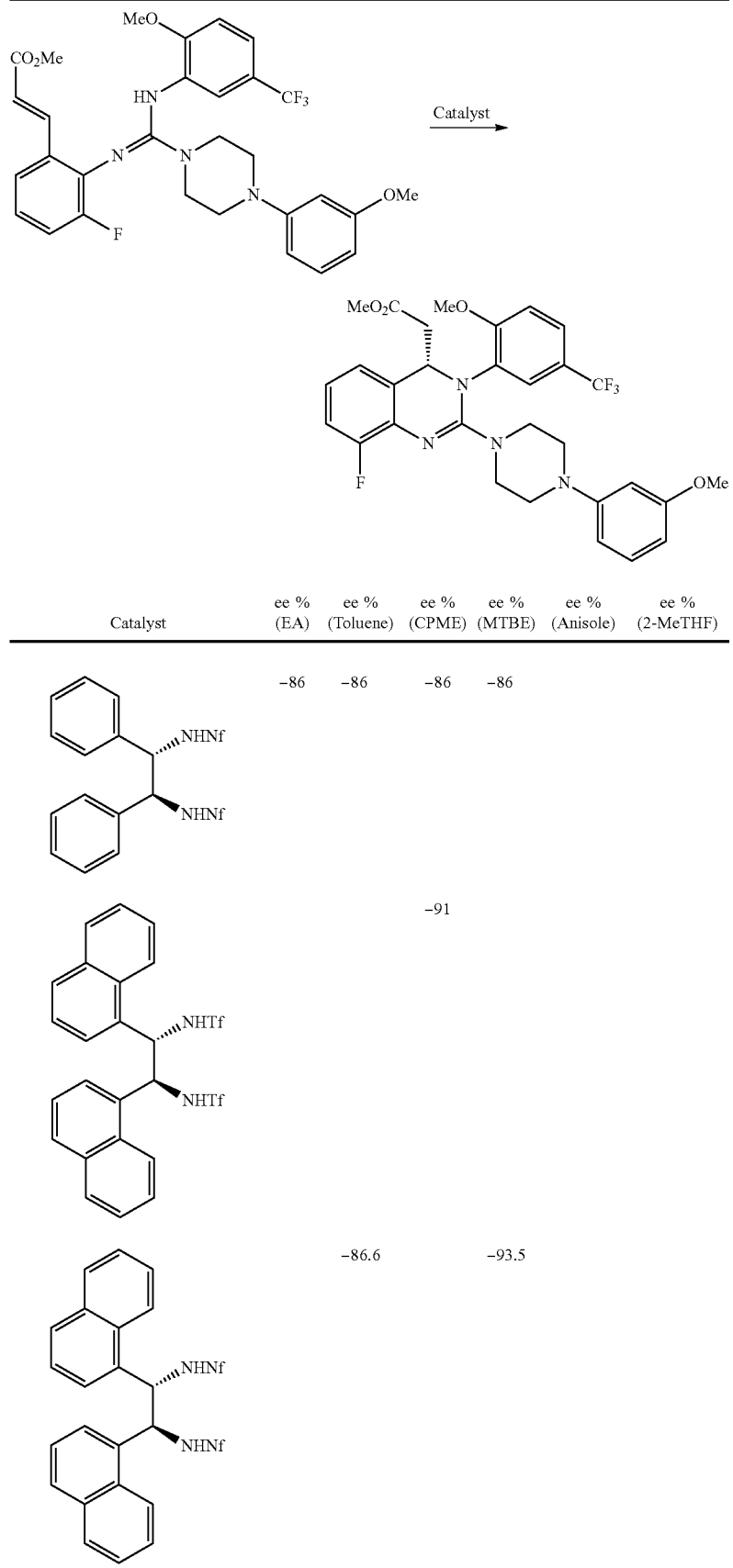
| Catalyst | ee % (EA) | ee % (Toluene) | ee % (CPME) | ee % (MTBE) | ee % (Anisole) | ee % (2-MeTHF) |
|---|---|---|---|---|---|---|
| (1,2-diphenyl-NHNf) | −86 | −86 | −86 | −86 | | |
| (1,2-di(1-naphthyl)-NHTf) | | −91 | | | | |
| (1,2-di(1-naphthyl)-NHNf) | | −86.6 | | −93.5 | | |

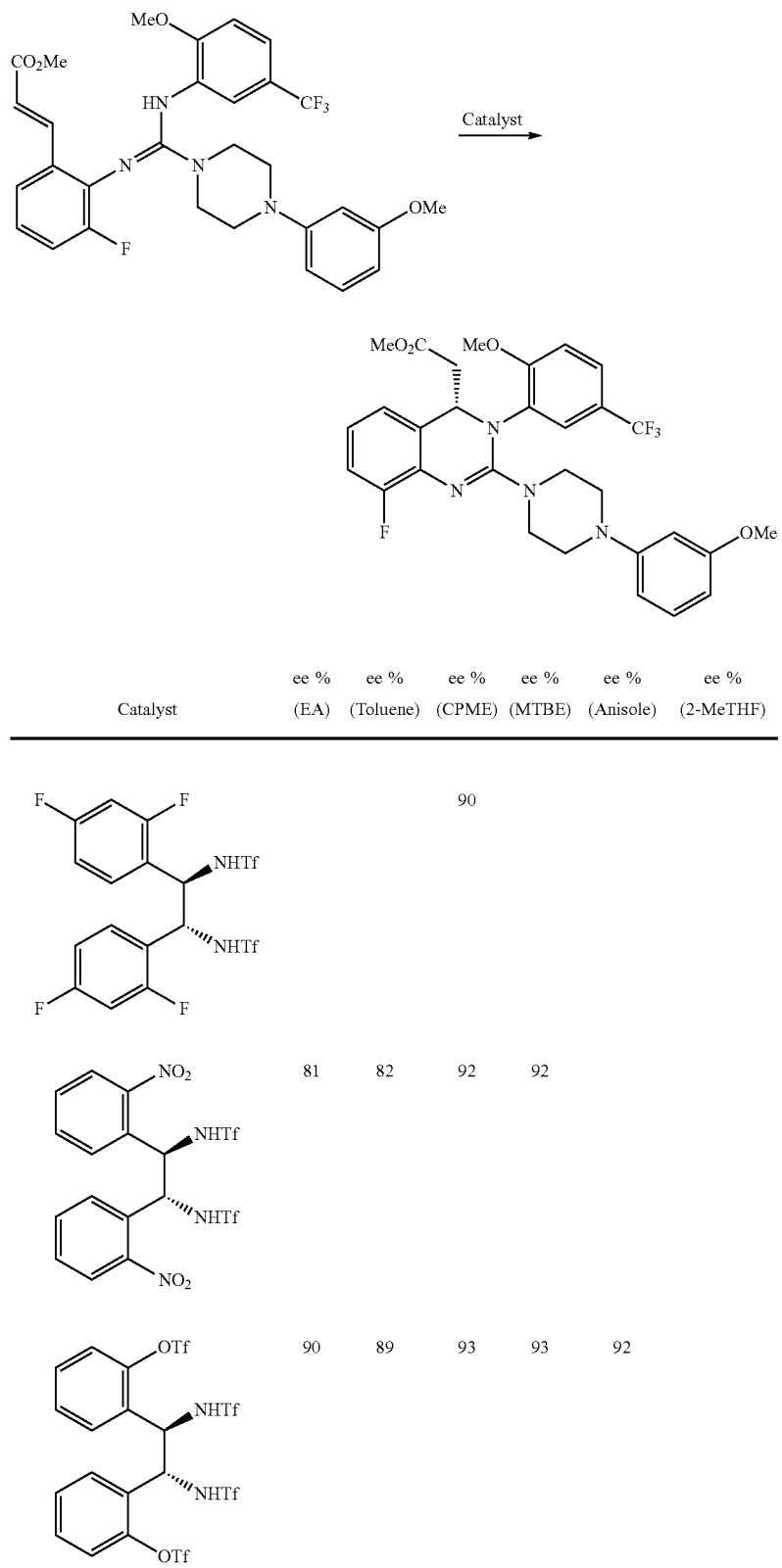
| Catalyst | ee % (EA) | ee % (Toluene) | ee % (CPME) | ee % (MTBE) | ee % (Anisole) | ee % (2-MeTHF) |
|---|---|---|---|---|---|---|
| (2,4-difluorophenyl bis-NHTf) | | | 90 | | | |
| (2-nitrophenyl bis-NHTf) | 81 | 82 | 92 | 92 | | |
| (2-OTf phenyl bis-NHTf) | 90 | 89 | 93 | 93 | 92 | |

-continued
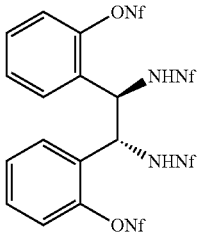
| Catalyst | ee % (EA) | ee % (Toluene) | ee % (CPME) | ee % (MTBE) | ee % (Anisole) | ee % (2-MeTHF) |
|---|---|---|---|---|---|---|
| 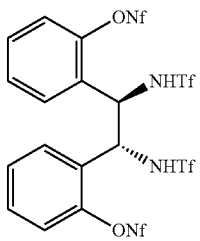 | 85 | 89 | 92 | 93 | | |
| 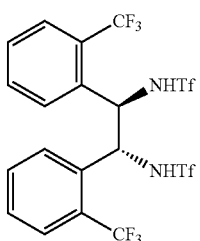 | 89 | 87 | 91 | 92 | | |
| 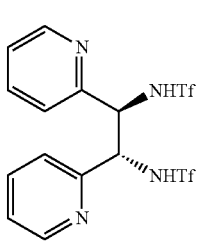 | 80 | 71 | 81 | 82 | | |
|  | 77 | 67 | 73 | | 73 | |

-continued
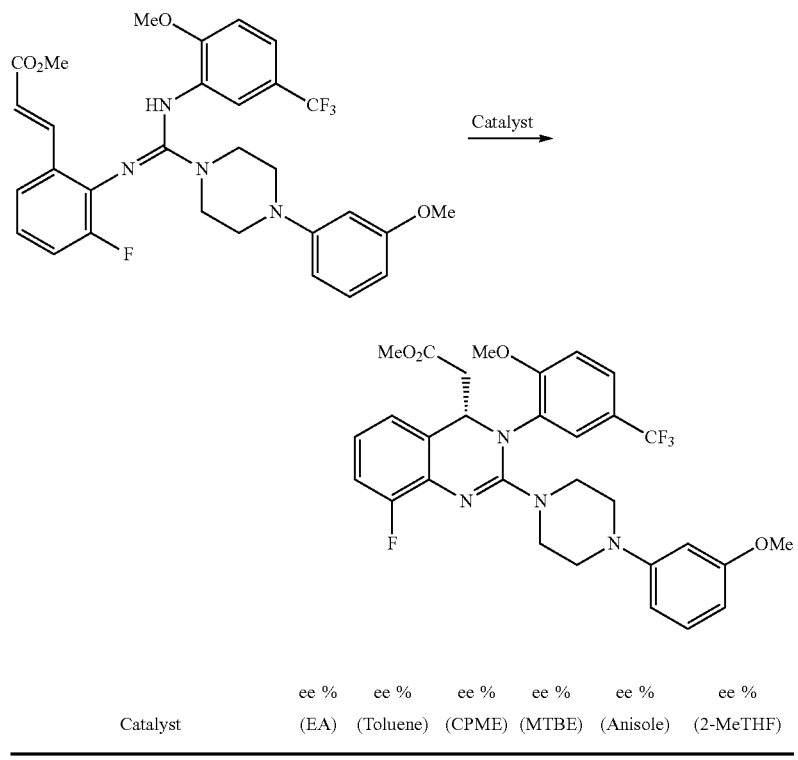
| Catalyst | ee % (EA) | ee % (Toluene) | ee % (CPME) | ee % (MTBE) | ee % (Anisole) | ee % (2-MeTHF) |
|---|---|---|---|---|---|---|
| 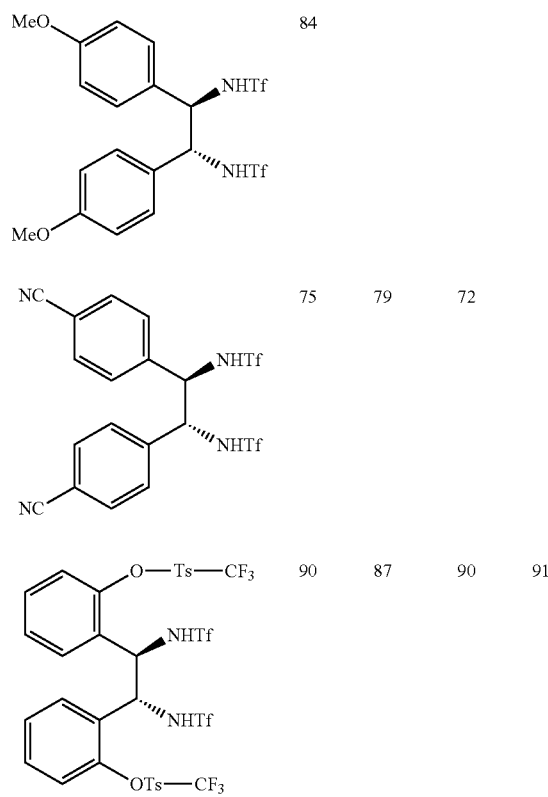 | 84 | | | | | |
| | 75 | 79 | 72 | | | |
| | 90 | 87 | 90 | 91 | | |

-continued

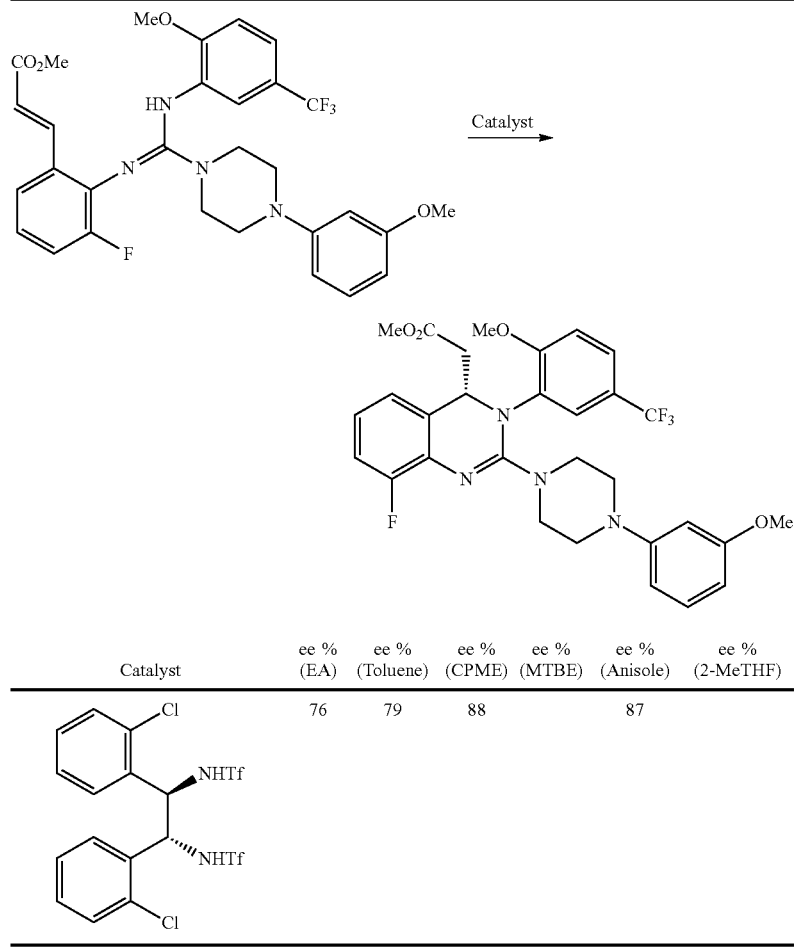

| Catalyst | ee % (EA) | ee % (Toluene) | ee % (CPME) | ee % (MTBE) | ee % (Anisole) | ee % (2-MeTHF) |
|---|---|---|---|---|---|---|
| (structure with 2-Cl phenyl, NHTf groups) | 76 | 79 | 88 | | 87 | |

In one embodiment, each reaction was carried out with a different catalyst shown in the following table at about 50° C. to about 80° C. using Cl-benzene as solvent. The corresponding % e.e.'s are included in the table.

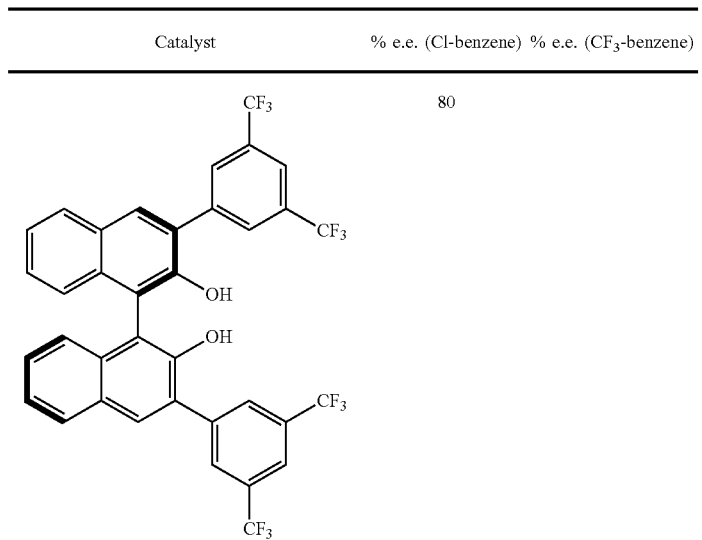

| Catalyst | % e.e. (Cl-benzene) | % e.e. (CF$_3$-benzene) |
|---|---|---|
| (BINOL with 3,5-bis(CF$_3$)phenyl groups) | | 80 |

-continued

| Catalyst | % e.e. (Cl-benzene) | % e.e. (CF₃-benzene) |
|---|---|---|
| *[structure: BINOL with 2,3,5,6-tetrafluoro-4-(trifluoromethyl)phenyl groups]* | 45 | |
| *[structure: BINOL with 3,5-difluorophenyl groups]* | 80 | |
| *[structure: BINOL with pentafluorophenyl groups]* | 40 | |

-continued
| Catalyst | % e.e. (Cl-benzene) | % e.e. (CF₃-benzene) |
|---|---|---|
| 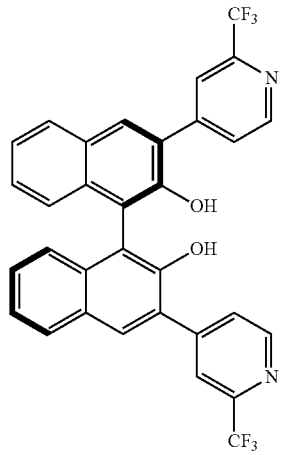 | | 72 |
| 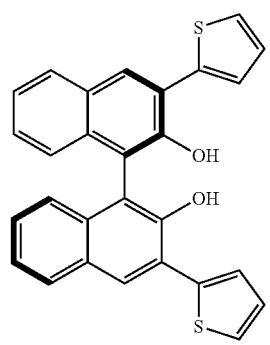 | | 72 |
| 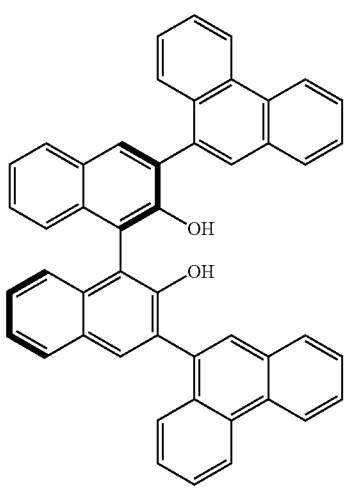 | | 77 |

In one embodiment, disclosed herein is a process for making a compound of Formula (II):

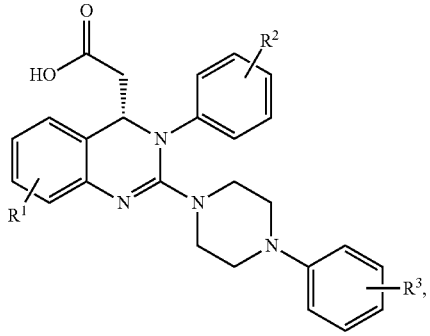

(II)

comprising the steps of:
(A) contacting a compound of formula (I):

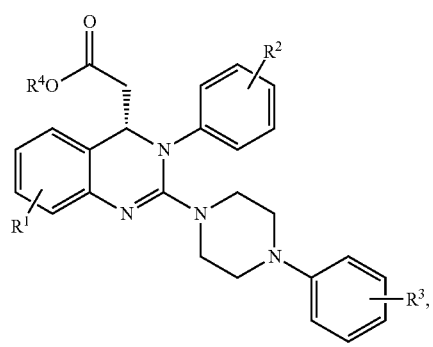

(I)

with di-p-toluoyl-D-tartaric acid in a mixture of organic solvent D and ethyl acetate for a time sufficient to form a compound of formula (ix):

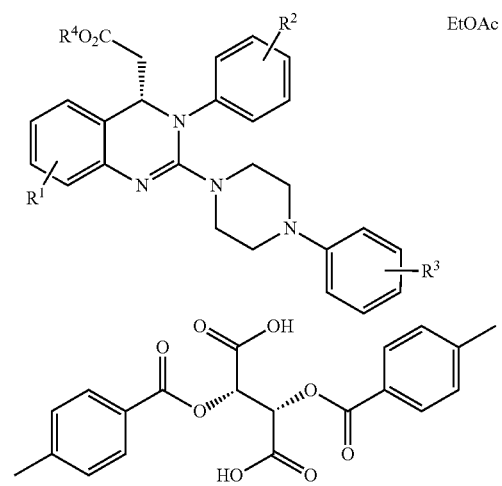

(ix)

wherein organic solvent D is selected from ethyl acetate, isopropyl acetate, THF, 2-methyltetrahydrofuran, DCM, benzene, toluene, xylene, chlorobenzene, dioxane, and a mixture thereof; and (B) (i) contacting the compound of Formula (ix) with a phosphate or hydrogen phosphate base in water; (ii) contacting the product of step (i) with an alkali metal hydroxide base in a mixture of water, an organic solvent D' and an organic solvent D"; (iii) acidifying the solution of step (ii) using an acid; and (iv) concentrating the solution of step (iii), taking up the concentrate in acetone, and adding the resulting solution to water and collecting the precipitate formed to provide a compound of Formula (II), wherein organic solvent D' is an organic alcohol, and organic solvent D" is an organic ether or THF, and wherein:

$R^1$ represents up to 3 phenyl group substituents, each independently selected from $C_1$-$C_6$ alkyl, $C_1$-$C_6$ haloalkyl, halo, —CN, —OH and $C_1$-$C_6$ alkoxy;

$R^2$ represents up to 3 phenyl group substituents, each independently selected from $C_1$-$C_6$ alkyl, $C_1$-$C_6$ haloalkyl, halo, —CN, —OH and $C_1$-$C_6$ alkoxy;

$R^3$ represents up to 3 phenyl group substituents, each independently selected from $C_1$-$C_6$ alkyl, $C_1$-$C_6$ haloalkyl, halo, —CN, —OH and $C_1$-$C_6$ alkoxy; and $R^4$ is selected from $C_1$-$C_6$ alkyl, and $C_3$-$C_7$ cycloalkyl.

In one embodiment of the above process, each occurrence of $R^1$ is halo; each occurrence of $R^2$ is independently selected from halo, $C_1$-$C_3$ alkyl, $C_1$-$C_3$ alkoxy and $C_1$-$C_3$ haloalkyl; each occurrence of $R^3$ is independently selected from $C_1$-$C_3$ alkyl and $C_1$-$C_3$ alkoxy; and $R^4$ is $C_1$-$C_6$ alkyl.

In one embodiment, the compound of formula (II) that is made by the above process is Compound A:

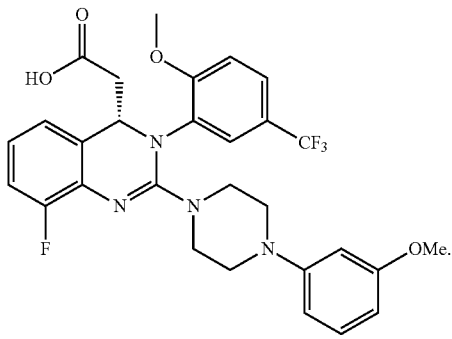 [SMILES: COc1cccc(N2CCN(C3=Nc4c(F)cccc4[C@H](CC(=O)O)N3c3cc(C(F)(F)F)ccc3OC)CC2)c1]

EXAMPLES

General Methods

Solvents, reagents, and intermediates that are commercially available were used as received. Reagents and intermediates that are not commercially available were prepared in the manner as described below. $^1$H NMR spectra were obtained on a Bruker Avance NMR Spectrometer and are reported as ppm downfield from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 minutes—10% CH$_3$CN, 5 minutes—95% CH$_3$CN, 5-7 minutes—95% CH$_3$CN, 7 minutes—stop. The retention time and observed parent ion are given.

Example 1: Preparation of Compound 3

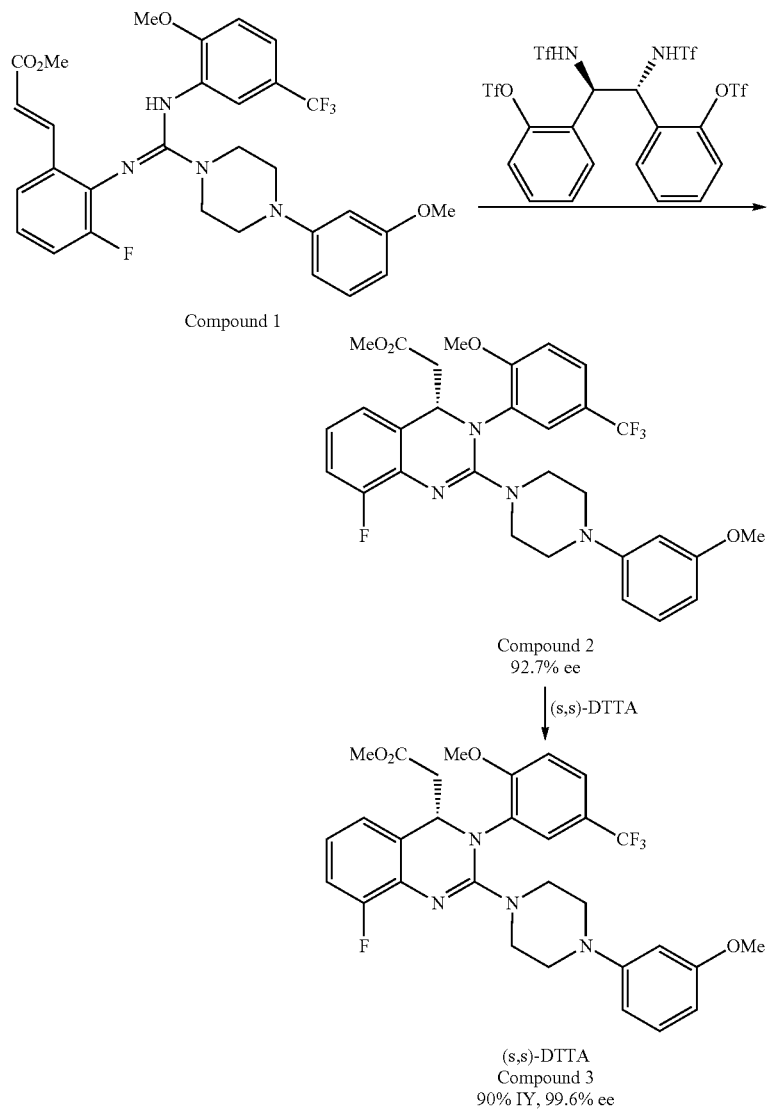

Compound 1 (4.05 g; 6.90 mmol) was charged into a 40 mL vial followed by the catalyst (0.285 g; 81 wt %; 0.299 mmol). To the mixture was charged MTBE (12 ml), and the slurry was heated at 35° C. HPLC was used to monitor the reaction and it indicated >99.9% conversion to Compound 2 after 24 hours with 92.7% ee. It was concentrated and solvent-switched to toluene. To the resulting toluene solution of crude reaction mixture (ca. 34 ml) was added (S,S)-DTTA (2.67 g; 6.90 mmol) in 6 mL EtOAc. The mixture was stirred at room temperature for 24 hours. The slurry was then filtered, and the collected solid was rinsed with EtOAc, and dried under vacuum to give 6.60 g (90% isolated yield) Compound 3 as its DTTA salt ethyl acetate solvate. $^1$H NMR (500 MHz, d$_6$-DMSO): $\delta_H$ 13.95 (2H, br s), 7.90 (4H, d, J=8.1 Hz), 7.55 (1H, dd, J=8.6, 1.3 Hz), 7.38 (4H, d, J=8.1 Hz), 7.26 (1H, d, J=7.8 Hz), 7.09-7.05 (3H, m), 6.91-6.86 (2H, m), 6.44 (1H, dd, J=8.2, 1.7 Hz), 6.39 (1H, t, J=2.0 Hz), 6.36 (1H, dd, J=8.2, 2.0 Hz), 5.82 (2H, s), 4.94 (1H, t, J=7.1 Hz), 4.02 (2H, q, J=7.1 Hz), 3.83 (3H, br s), 3.68 (3H, s), 3.64 (3H, s), 3.47 (2H, br s), 3.37 (2H, br s), 2.95 (2H, br s), 2.87-2.80 (3H, m), 2.56 (1H, dd, J=14.3, 7.0 Hz), 2.39 (6H, s), 1.98 (3H, s), 1.17 (3H, t, J=7.1 Hz).

Example 2: Preparation of Compound 3

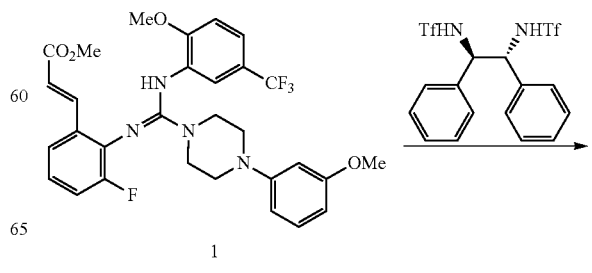

1

-continued

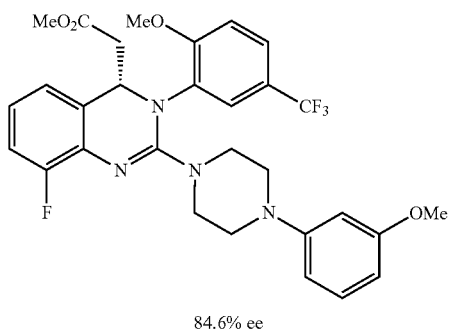

84.6% ee

↓ (s,s)-DTTA

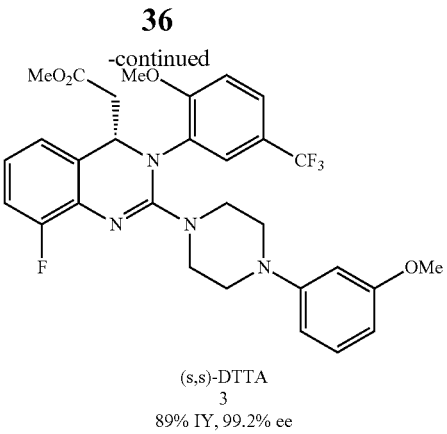

(s,s)-DTTA
3
89% IY, 99.2% ee

Compound 1 (5.00 g, 8.52 mmol) was charged into a 40-mL vial followed by catalyst (0.207 g, 0.426 mmol). To the mixture was charged MTBE (15 ml), and the slurry was then heated at 50° C. HPLC was used to monitor the reaction and it indicated >99.9% conversion after 24 hours with 84.6% ee. It was concentrated and solvent-switched to toluene. To the toluene solution of crude reaction mixture (ca. 40 ml) was added (s,s)-DTTA (3.36 g; 8.52 mmol) in 5 mL EtOAc. The mixture was stirred and aged at room temperature for 24 hours. The white slurry was filtered and the collected solid was rinsed with EtOAc, and dried under vacuum to give 8.05 g (89% isolated yield) Compound 3 as its DTTA salt ethyl acetate solvate.

Example 3: Preparation of Compound 3

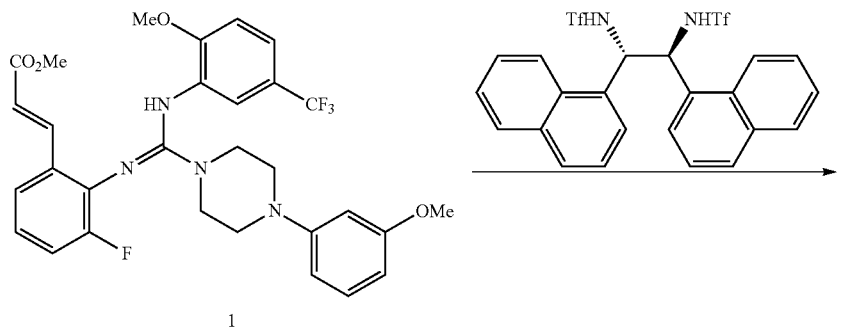

1

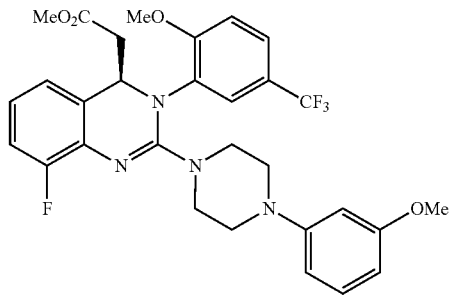

−84.8% ee

↓ (r,r)-DTTA

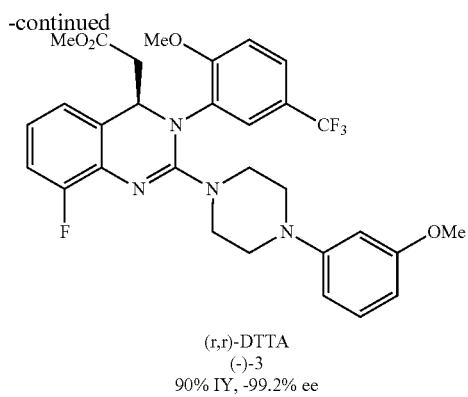

(r,r)-DTTA
(−)-3
90% IY, -99.2% ee

Compound 1 (4.00 g; 6.82 mmol) and catalyst (0.29 g; 0.50 mmol) were charged into a 100-mL three-neck round-bottom flask equipped with a condenser and an overhead stirrer. To the mixture was charged toluene (32 ml), and the slurry was then heated at 35° C. HPLC was used to monitor the reaction and it indicated >99.9% conversion after 36 hours with −84.8% ee. At 35° C., to the clear reaction mixture was added (R,R)-DTTA (2.63 g; 6.82 mmol) in 8 mL EtOAc. The mixture was cooled to 2-3° C. over 5 hours and then aged at 2-3° C. overnight. The slurry was filtered, and the collected solid was rinsed with EtOAc. The wet cake was dried to give 6.48 g (90% isolated yield) Compound (−)-3 as its DTTA salt ethyl acetate solvate Example 4: Preparation of Compound 2

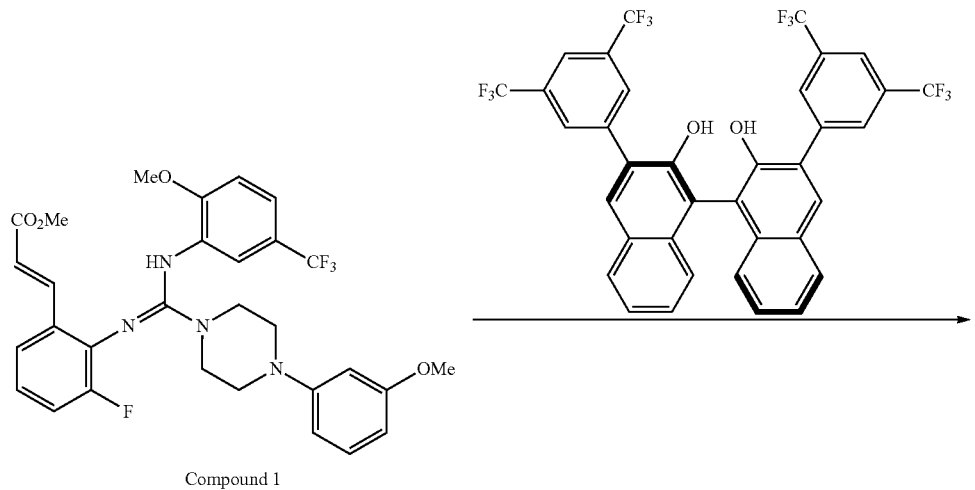

Compound 1

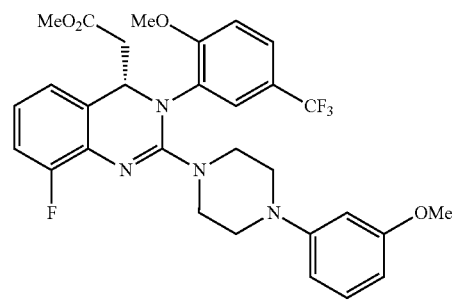

Compound 2
95% yield, 80% ee

Compound 1 (1 g; 1.7 mmol) was charged into a 40-mL vial followed by catalyst (0.121 g; 0.17 mmol). To the mixture was charged CF$_3$-benzene (10 ml), and the reaction was then heated at 50° C. Compound 2 was obtained after 66 hours with 95% conversion and 80% e.e.

Catalyst Preparations

In one embodiment, the bistriflate catalyst having the following structure can be obtained from Oakwood Products, Inc. at 730 Columbia Hwy. N, Estill, S.C. 29918.

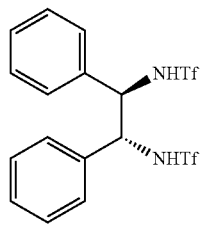

In one embodiment, a process for preparing the following catalyst is shown below.

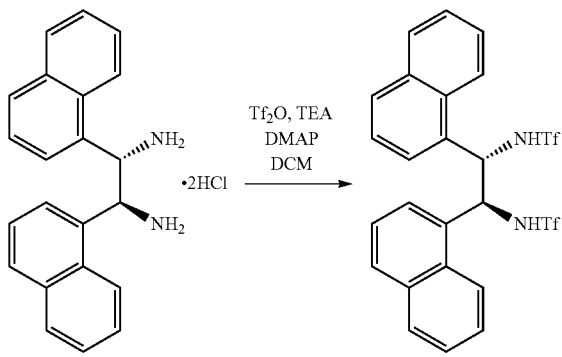

To a cooled solution of diamine HCl salt (0.22 g, 0.57 mmol) in DCM (4.4 ml) was added TEA (5.0 eq, 0.29 g, 2.85 mmol) and DMAP (0.1 eq, 7 mg, 0.057 mmol). To the resulting mixture was added Tf$_2$O solution in DCM (1M, 2.2 eq, 1.26 ml) dropwise maintaining the reaction temperature below −50° C. After stirring at the same temperature for 10 min, the reaction mixture was allowed to warm to room temperature slowly over 30 min. The reaction was poured into 4% NaHCO$_3$ aq. solution and extracted with DCM (5 ml×2). The combined organic layer was washed with 1N HCl followed by brine. After drying over Na$_2$SO$_4$, the crude product was purified by column chromatography on silica to afford the desired bistriflate as a white solid (0.28 g, 0.48 mmol, Y=84%). $^1$H NMR (500 MHz, DMSO-d$_6$) δ 10.75 (s, 2H), 7.95 (d, J=7.3 Hz, 4H), 7.59 (d, J=8.1 Hz, 2H), 7.46 (d, J=8.1 Hz, 4H), 7.31 (t, J=7.5 Hz, 2H), 7.16 (t, J=7.7 Hz, 2H), 5.95 (s, 2H). $^{13}$C NMR (101 MHz, DMSO-d$_6$) δ 133.4, 132.3, 129.7, 128.3, 128.3, 125.9, 125.3, 125.2, 124.6, 122.2, 119.0 (q, J=322.1 Hz), 57.4. $^{19}$F NMR (471 MHz, DMSO-d$_6$) δ −77.78.

In one embodiment, a process for preparing the following catalyst is shown below.

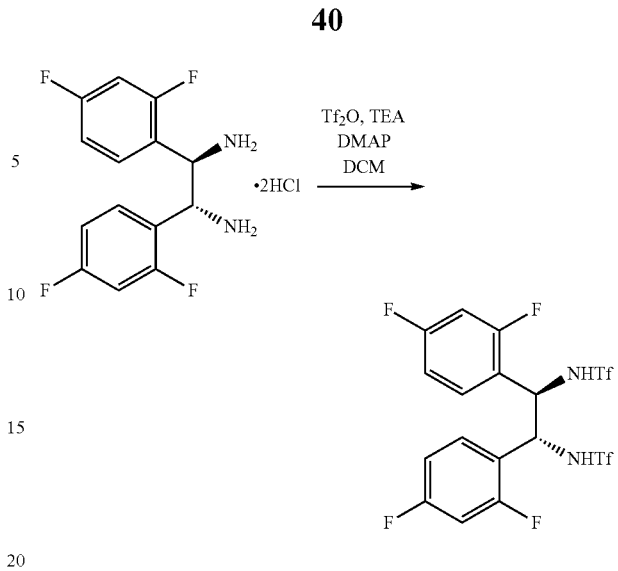

Following a similar procedure as the above example, diamine HCl salt (0.52 g, 1.45 mmol) was transformed to bistriflate (0.55 g, 1.00 mmol, Y=69%) as white solid. $^1$H NMR (500 MHz, DMSO-d$_6$) δ 10.75 (s, 2H), 7.72 (q, J=8.0 Hz, 2H), 7.13 (td, J=8.5, 2.6 Hz, 2H), 7.05-6.96 (m, 2H), 5.09 (d, J=3.5 Hz, 2H). $^{13}$C NMR (101 MHz, DMSO-d$_6$) δ 162.5 (dd, J=248.4, 12.4 Hz), 158.9 (dd, J=248.5, 12.4 Hz), 130.2 (d, J=8.6 Hz), 121.1 (q ??), 121.0 (d, J=13.9 Hz), 112.6 (d, J=21.5 Hz), 103.7 (t, J=26.4 Hz), 55.0. $^{19}$F NMR (471 MHz, DMSO-d$_6$) δ −77.90, −108.69, −113.47.

In one embodiment, a process for preparing the following catalyst is shown below.

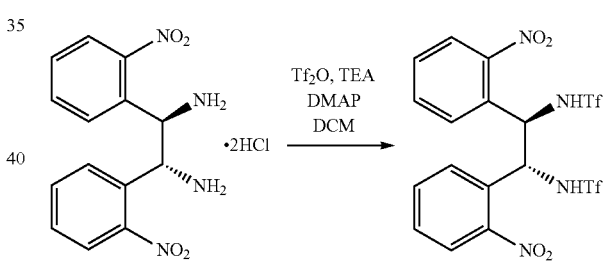

Following a similar procedure as the above example, diamine HCl salt (0.2 g, 0.53 mmol) was transformed to bistriflate (0.2 g, 0.35 mmol, Y=66%) as white solid. $^1$H NMR (500 MHz, DMSO-d$_6$) δ 10.98 (s, 2H), 7.97 (q, J=7.8 Hz, 2H), 7.72 (td, J=7.8, 1.3 Hz, 2H), 7.66 (dd, J=8.2, 1.3 Hz, 2H), 7.47 (td, J=8.0, 1.3 Hz, 2H), 5.87 (s, 2H). $^{13}$C NMR (125 MHz, DMSO-d$_6$) δ 147.6, 134.6, 130.9, 130.6, 129.6, 125.1, 119.5 (q, J=318.7 Hz), 56.8. $^{19}$F NMR (470 MHz, DMSO-d$_6$) δ −77.80.

In one embodiment, a process for preparing the following catalyst is shown below.

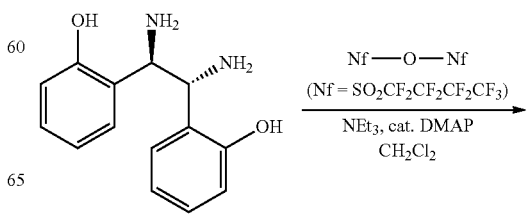

-continued

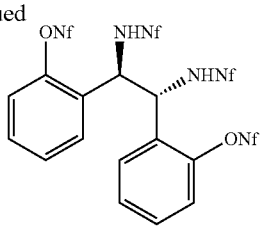

To a stirring mixture of diamine compound (0.200 g, 0.819 mmol), NEt₃ (0.340 g, 3.36 mmol), DMAP (0.0020 g, 0.016 mmol) and CH₂Cl₂ (7 ml) chilled to less than −40° C. was added dropwise nonafluorobutanesulfonic anhydride (1.95 g, 3.36 mmol). When complete the reaction mixture was poured into a 1:1 mixture of saturated NaHCO₃ and water. The organic layer was separated and the aqueous layer was extracted with CH₂Cl₂. The organic layers were combined and washed with 1N HCl and water, dried with Na₂SO₄ and filtered. The filtrate was concentrated under vacuum and purified on silica to give catalyst as a solid (0.689 g, 0.819 mmol, Y=61%). ¹H NMR (500 MHz, acetonitrile-d₃): δ 8.21 (br s, 2H), 7.79 (dd, J=7.8 Hz, 1.3 Hz, 2H), 7.48 (t, J=7.6 Hz, 2H), 7.42 (t, J=8.5 Hz, 2H), 7.10 (d, J=8.3 Hz, 2H), 5.30 (s, 2H). ¹³C NMR (126 MHz, DMSO-d₆): δ 146.1, 131.5, 129.2, 129.0, 128.1, 120.1, 56.8 [High order coupling of Nf cannot be resolved due to signal to noise ratio]. ¹⁹F NMR (471 MHz, DMSO-d₆): δ −81.5 (t, J=9.4 Hz), −81.7 (t, J=9.4 Hz), −110.0 (m), −113.5 (t, J=9.4 Hz), −121.4, −121.8, −126.3 (t, J=14.1 Hz), −126.7 (t, J=14.1 Hz).

In one embodiment, a process for preparing the following catalyst is shown below.

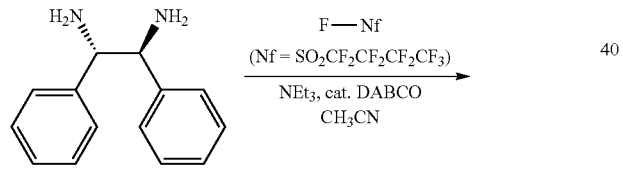

To a stirring mixture containing a diamine compound (0.500 g, 2.36 mmol), NEt₃ (0.953 g, 9.42 mmol), DABCO (0.013 g, 0.12 mmol) and acetonitrile (8 ml) cooled in an ice bath was added dropwise perfluoro-1-butanesulfonyl fluoride (1.71 g, 5.65 mmol). When complete the reaction was poured into 1:1 mixture of saturated NaHCO₃ and water and extracted with ethyl acetate. The aqueous layer was cut away and the organic layer was washed with 1N HCl and water, dried with sodium sulfate and filtered. The filtrate was concentrated under vacuum and purified on silica to give catalyst as a solid (1.34 g, 1.73 mmol, Y=73%). ¹H NMR (500 MHz, DMSO-d₆): 10.51 (br s, 2H), 7.14-7.09 (m, 10H), 4.73-4.71 (m, 2H). ¹³C NMR (126 MHz, DMSO-d₆): δ 137.4, 128.0, 127.7, 127.3, 64.1 [Higher order coupling of Nf cannot be resolved due to signal to noise ratio]. ¹⁹F NMR (471 MHz, DMSO-d₆): δ −80.6 (t, J=9.4 Hz), −113.4 (t, J=9.4 Hz), −121.1 (d, J=9.4 Hz), −125.9 (t, J=9.4 Hz).

In one embodiment, a process for preparing the following catalyst is shown below.

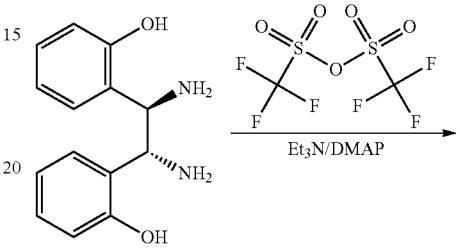

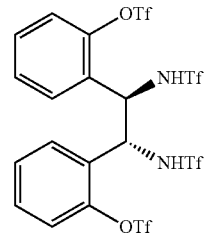

2,2'-((1R,2R)-1,2-Diaminoethane-1,2-diyl)diphenol (5.0 g, 19.4 mmol) was charged into a 250-mL round-bottom flask followed by DCM (125 ml). To the resulting suspension was charged Et₃N (13.6 mL; 97.0 mmol) and the mixture was cooled to −10° C. Tf₂O (13.1 mL; 78.0 mmol) was charged slowly to maintain the internal temperature lower than 0° C. The mixture was then warmed up to room temperature and aged for 0.5 h. The reaction mixture was then poured into 4% aq. NaHCO₃ solution. The organic phase was washed with 1N aq. HCl and then brine. Final organic phase was dried over Na₂SO₄ and then concentrated. The resulting crude residue was purified by silica gel chromatography to afford the desired product in an 81% (16 g) as an ethyl acetate solvate. ¹H NMR (500 MHz, d₆-DMSO): δ$_H$ 11.14 (2H, br s), 8.01-8.03 (2H, dd, J=7.5, 2.0 Hz), 7.42-7.50 (4H, m), 7.06-7.07 (2H, d, J=8.0 Hz), 5.09 (2H, br s), 4.02-4.06 (4H, q, J=7.2 Hz, EtOAc), 2.00 (6h, s, EtOAc), 1.17-1.20 (6H, t, J=7.2 Hz, EtOAc). ¹³C NMR (126 MHz, d₆-DMSO): δc 145.15, 131.32, 129.68, 128.46, 128.18, 119.31, 119.02 (q, J=322 Hz), 117.66 (q, J=321 Hz), 55.94. ¹⁹F NMR (471 MHz, d₆-DMSO): δ$_F$ −74.24, −77.80.

Preparation of Compound A

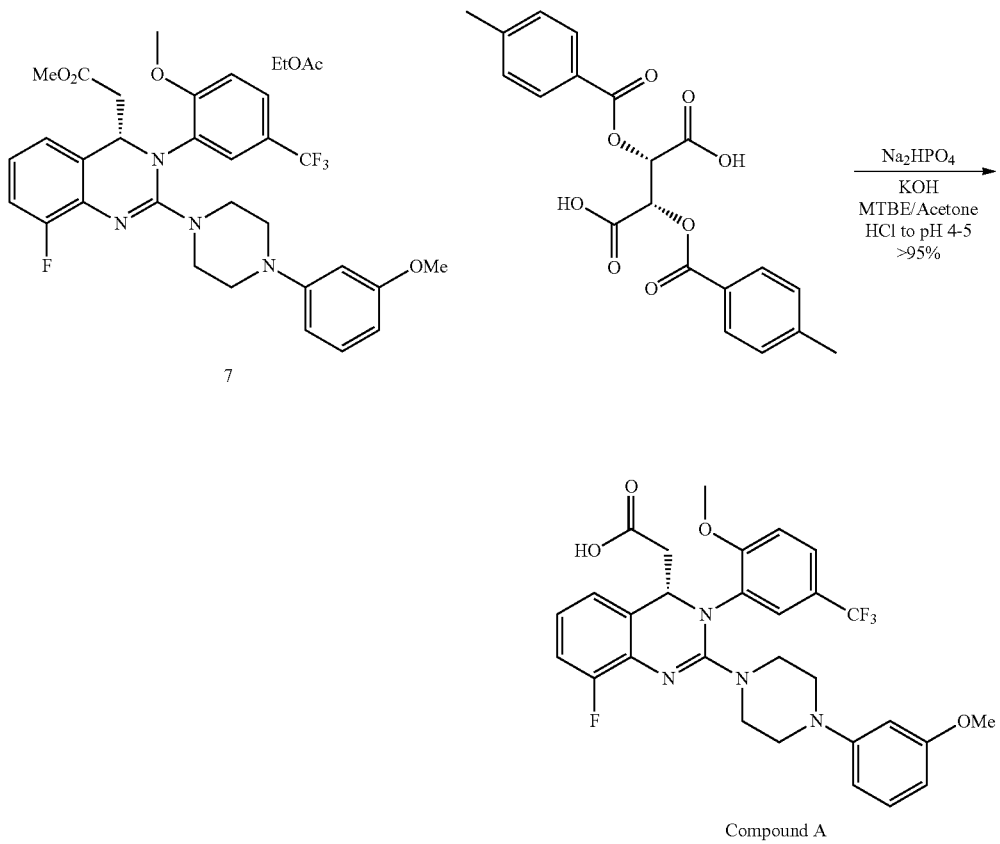

To a slurry of compound 7 (20 g, 18.9 mmol) in MTBE (40 mL) at room temperature was added a solution of sodium phosphate dibasic dihydrate (8.42 g, 47.3 mmol) in water (80 mL) and the resulting slurry was allowed to stir at room temperature for 40 minutes. The reaction mixture was transferred to a separatory funnel and the organic phase was collected and washed with a solution of sodium phosphate dibasic dihydrate (3.37 g, 18.91 mmol) in water (40 mL). A solution of KOH (4.99 g, 76 mmol) in water (80 mL) and methanol (10 mL) was then added to the organic phase and the resulting mixture was heated to 50° C. and allowed to stir at this temperature for 6 hours. MTBE (20 mL) and water (40 mL) were then added to the reaction mixture and the resulting solution was transferred to a separatory funnel and the aqueous layer was collected and washed with MTBE (20 mL). Additional MTBE (40 mL) was added to the aqueous layer and the resulting solution was adjusted to pH 4-5 via slow addition of concentrated HCl. The resulting acidified solution was transferred to a separatory funnel and the organic phase was collected, concentrated in vacuo and solvent switched with acetone, maintaining a 30 mL volume. The resulting acetone solution was added dropwise to water and the precipitate formed was filtered to provide compound A as a white solid (10 g, 92%). $^1$H NMR (500 MHz, d$_6$-DMSO): δ$_H$ 12.6 (1H, s), 7.52 (1H, dd, J=8.6, 1.3 Hz), 7.41 (1H, brs), 7.22 (1H, d, J=7.2 Hz), 7.08-7.02 (2H, m), 6.87-6.84 (2H, m), 6.44 (1H, dd, J=8.3, 1.8 Hz), 6.39 (1H, t, J=2.1 Hz), 6.35 (1H, dd, J=8.1, 2.0 Hz), 4.89 (1H, t, J=7.3 Hz), 3.79 (3H, br s), 3.68 (3H, s), 3.47 (2H, br s), 3.39 (2H, br s), 2.96-2.93 (2H, m), 2.82-2.77 (3H, m), 2.44 (1H, dd, J=14.8, 7.4 Hz).

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entirety into the disclosure.

What is claimed is:
1. A process for preparing a compound of Formula (I):

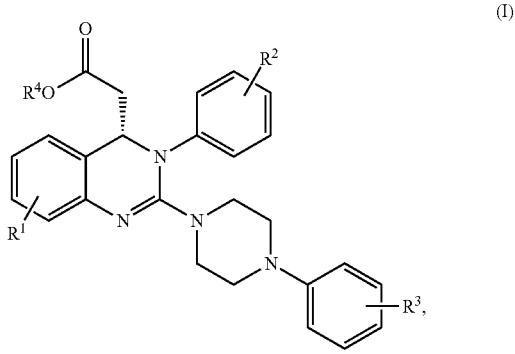

or a salt thereof, comprising contacting a compound of formula (viii):

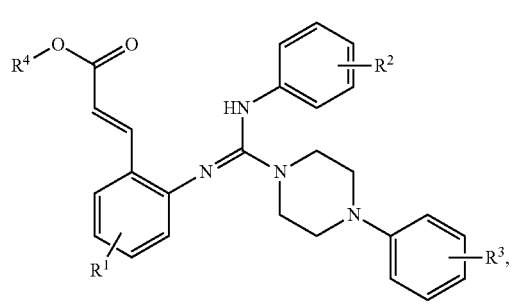

or a salt thereof, with a catalyst of formula (V):

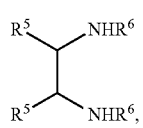

wherein each occurrence of $R^5$ is independently selected from the group consisting of phenyl; naphthyl and pyridine; wherein each of the phenyl and naphthyl is optionally substituted with one to three substituents independently selected from halogen, —O—$C_1$-$C_4$alkyl, —CN, —$NO_2$, —O-Tf, and $C_1$-$C_4$alkyl, wherein $C_1$-$C_4$ alkyl can be optionally substituted with one to four halogens; and each occurrence of $R^6$ is independently selected from the group consisting of Tf and Nf;

in a suitable solvent for a time sufficient to form a compound of formula (I);

wherein:

$R^1$ represents up to 3 phenyl group substituents, each independently selected from $C_1$-$C_6$ alkyl, $C_1$-$C_6$ haloalkyl, halo, —CN, —OH and $C_1$-$C_6$ alkoxy;

$R^2$ represents up to 3 phenyl group substituents, each independently selected from $C_1$-$C_6$ alkyl, $C_1$-$C_6$ haloalkyl, halo, —CN, —OH and $C_1$-$C_6$ alkoxy;

$R^3$ represents up to 3 phenyl group substituents, each independently selected from $C_1$-$C_6$ alkyl, $C_1$-$C_6$ haloalkyl, halo, —CN, —OH and $C_1$-$C_6$ alkoxy; and $R^4$ is $C_1$-$C_6$ alkyl or $C_3$-$C_7$ cycloalkyl.

2. The process of claim 1, wherein the catalyst is a compound of formula (Va):

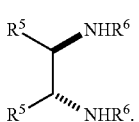

3. The process of claim 1, wherein each occurrence of $R^1$ is halo; each occurrence of $R^2$ is independently selected from halo, $C_1$-$C_3$ alkyl, $C_1$-$C_3$ alkoxy and $C_1$-$C_3$ haloalkyl; each occurrence of $R^3$ is independently selected from $C_1$-$C_3$ alkyl and $C_1$-$C_3$ alkoxy; and $R^4$ is $C_1$-$C_6$ alkyl.

4. The process of claim 1, wherein the catalyst is selected from the group consisting of:

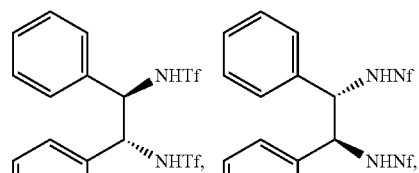
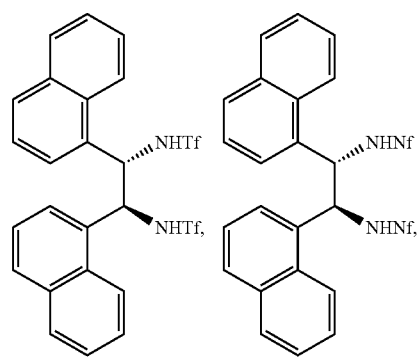
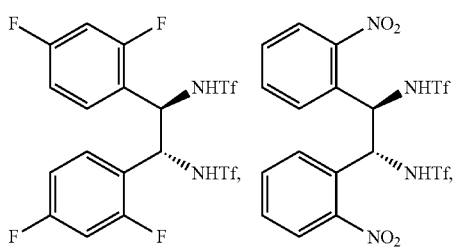
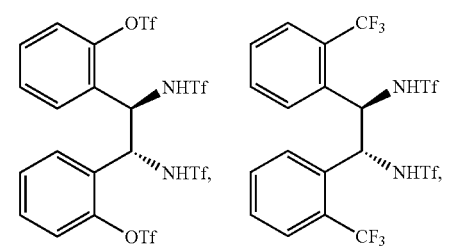
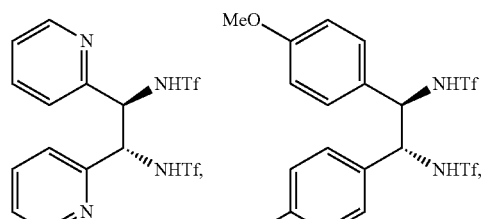
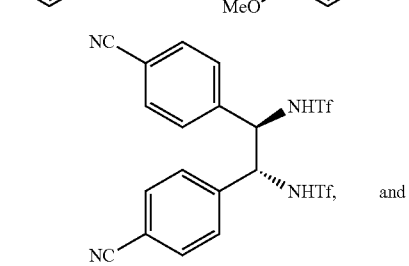

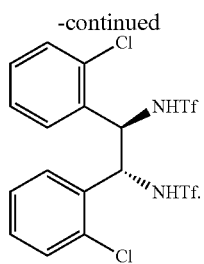

5. The process of claim 1, wherein the catalyst is selected from the group consisting of:

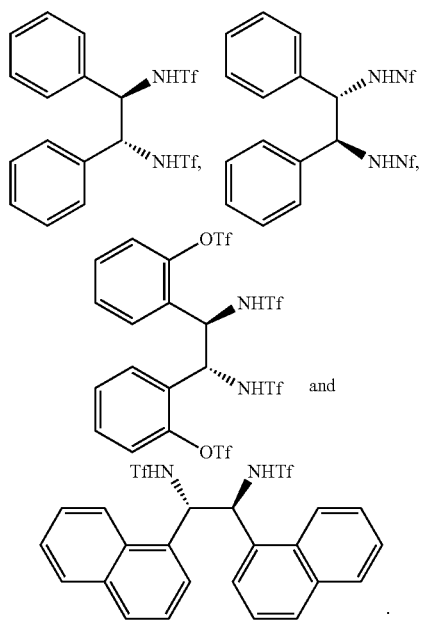

6. The process of claim 1, wherein the solvent is selected from the group consisting of acetone, toluene, dichloromethane, DCE, THF, chlorobenzene, 1,2-dichlorobenzene, MTBE, CPME, acetonitrile, EtOAc, IPAc, MeOAc, nitromethane, trifluoromethylbenzene, methyl ethyl ketone, DME, anisole, hexafluorobenzene, o-xylene, fluorobenzene, 1,4-dioxane, iPr$_2$O and 2-MeTHF.

7. The process of claim 6, wherein the solvent is selected from toluene, MTBE, and CPME.

8. The process of claim 1, wherein said process is carried out at a temperature from about 20° C. to about 60° C.

9. A process for preparing a compound of Formula (I):

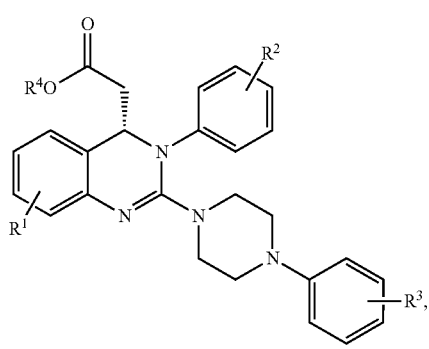

or a salt thereof, comprising contacting a compound of formula (viii):

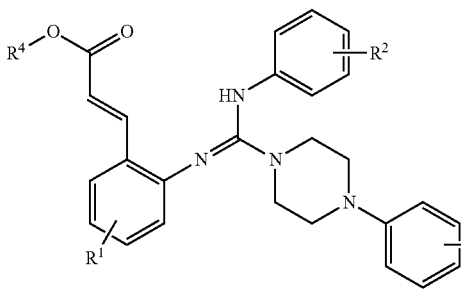

or a salt thereof, with a catalyst of formula (VI):

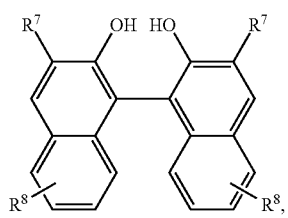

wherein each occurrence of $R^7$ is independently selected from the group consisting of phenyl, naphthyl, phenanthrenyl, pyridyl and thiophenyl, each of which is optionally substituted with one to five substituents independently selected from halogen and —CF$_3$; and each occurrence of $R^8$ is hydrogen;

in a suitable solvent for a time sufficient to form a compound of formula (I);

wherein:

$R^1$ represents up to 3 phenyl group substituents, each independently selected from C$_1$-C$_6$ alkyl, C$_1$-C$_6$ haloalkyl, halo, —CN, —OH and C$_1$-C$_6$ alkoxy;

$R^2$ represents up to 3 phenyl group substituents, each independently selected from C$_1$-C$_6$ alkyl, C$_1$-C$_6$ haloalkyl, halo, —CN, —OH and C$_1$-C$_6$ alkoxy;

$R^3$ represents up to 3 phenyl group substituents, each independently selected from C$_1$-C$_6$ alkyl, C$_1$-C$_6$ haloalkyl, halo, —CN, —OH and C$_1$-C$_6$ alkoxy; and $R^4$ is C$_1$-C$_6$ alkyl or C$_3$-C$_7$ cycloalkyl.

10. The process of claim 9, wherein each occurrence of $R^1$ is halo; each occurrence of $R^2$ is independently selected from halo, C$_1$-C$_3$ alkyl, C$_1$-C$_3$ alkoxy and C$_1$-C$_3$ haloalkyl; each occurrence of $R^3$ is independently selected from C$_1$-C$_3$ alkyl and C$_1$-C$_3$ alkoxy; and $R^4$ is C$_1$-C$_6$ alkyl.

11. The process of claim 9, wherein the catalyst is selected from the group consisting of:

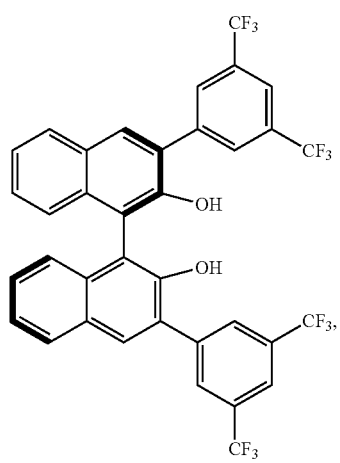
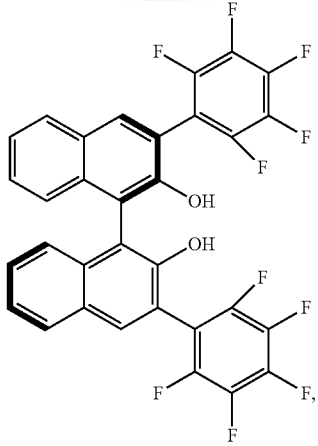

12. The process of claim 9, wherein the catalyst is selected from the group consisting of:

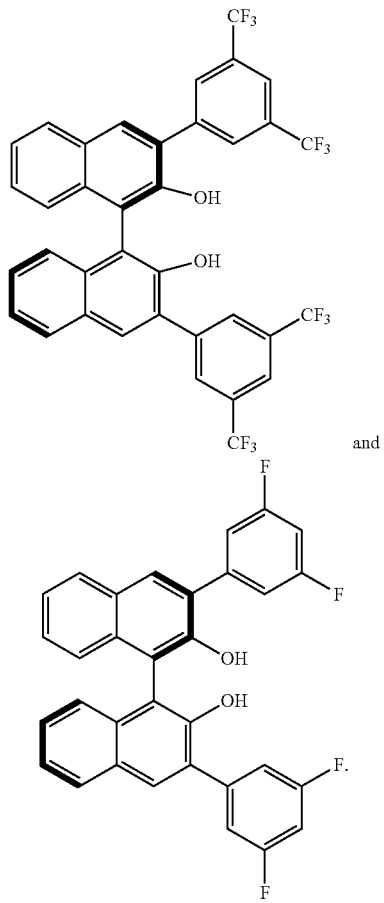

and

13. The process of claim 9, wherein the solvent is selected from the group consisting of CF$_3$-toluene, Cl-benzene, and 1,2-Cl$_2$-benzene.

14. The process of claim 9, wherein said process is carried out at a temperature from about 50° C. to about 80° C.

15. The process of claim 1, wherein the compound of formula (I) made by said process is:

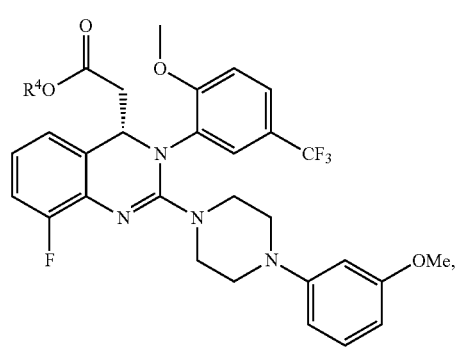

wherein R$^4$ is C$_1$-C$_6$ alkyl.

16. The process of claim 1, wherein the compound made by said process is Compound (III):

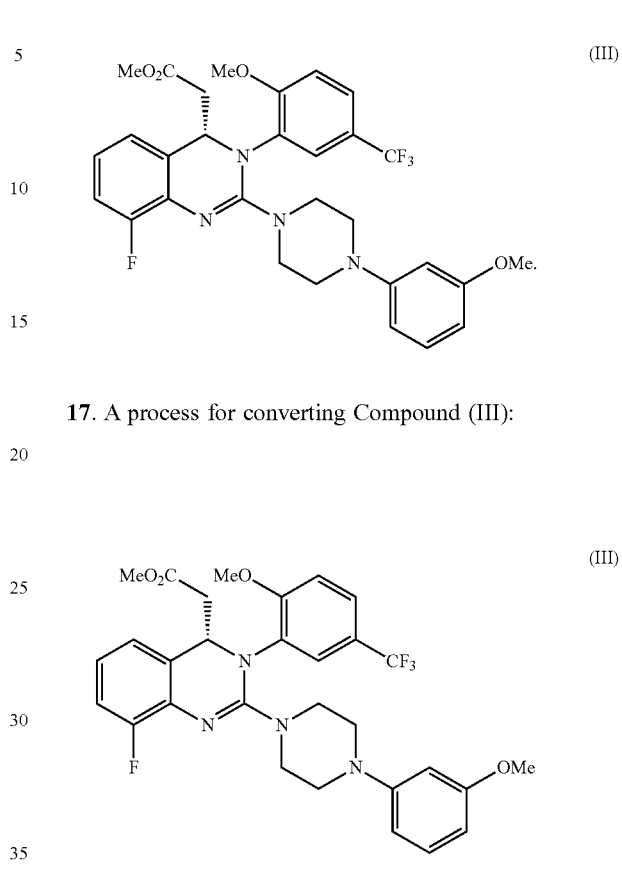

17. A process for converting Compound (III):

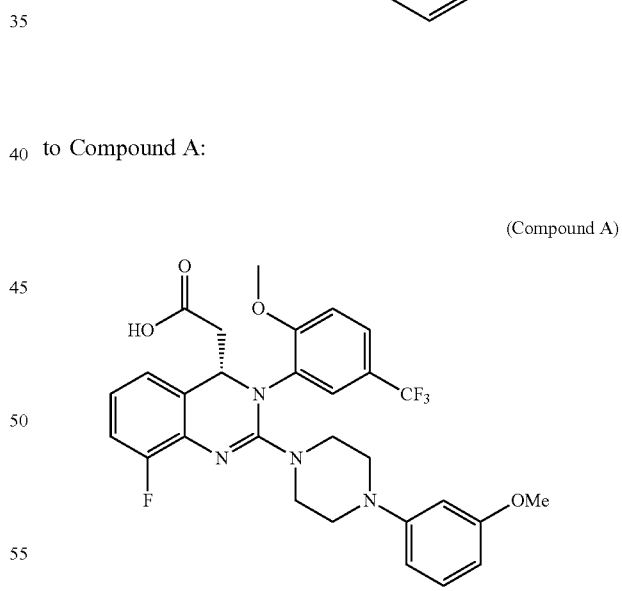

to Compound A:

(Compound A)

the method comprising hydrolyzing the methyl ester group of compound (III).

* * * * *

EX PARTE REEXAMINATION CERTIFICATE (13043rd)

United States Patent
Chung et al.

(10) Number: US 10,392,353 C1
(45) Certificate Issued: Sep. 30, 2025

(54) PROCESSES FOR MAKING SUBSTITUTED QUINAZOLINE COMPOUNDS USING HYDROGEN BONDING CATALYSTS

(71) Applicants: Merck Sharp & Dohme Corp., Rahway, NJ (US); Cheol K. Chung, Westfield, NJ (US); Guy R. Humphrey, Hillsborough, NJ (US); Zhijian Liu, Kendall Park, NJ (US); Mark McLaughlin, Summit, NJ (US); Yingju Xu, Edison, NJ (US); Younong Yu, East Brunswick, NJ (US)

(72) Inventors: Cheol K. Chung, Westfield, NJ (US); Guy R. Humphrey, Hillsborough, NJ (US); Zhijian Liu, Kendall Park, NJ (US); Mark McLaughlin, Summit, NJ (US); Yingju Xu, Edison, NJ (US); Younong Yu, East Brunswick, NJ (US)

(73) Assignee: MERCK SHARP & DOHME LLC, Rahway, NJ (US)

Reexamination Request:
No. 90/019,744, Nov. 26, 2024

Reexamination Certificate for:
Patent No.: 10,392,353
Issued: Aug. 27, 2019
Appl. No.: 15/778,505
PCT Filed: Nov. 18, 2016
PCT No.: PCT/US2016/062654
§ 371 (c)(1),
(2) Date: May 23, 2018
PCT Pub. No.: WO2017/091453
PCT Pub. Date: Jun. 1, 2017

Related U.S. Application Data

(60) Provisional application No. 62/259,167, filed on Nov. 24, 2015.

(51) Int. Cl.
*C07D 239/84* (2006.01)

(52) U.S. Cl.
CPC ..................... *C07D 239/84* (2013.01)

(58) Field of Classification Search
None
See application file for complete search history.

(56) References Cited

To view the complete listing of prior art documents cited during the proceeding for Reexamination Control Number 90/019,744, please refer to the USPTO's Patent Electronic System.

*Primary Examiner* — Alan D Diamond

(57) ABSTRACT

Disclosed herein is a novel process for preparing substituted quinazoline compounds of formula (I) using a hydrogen bonding catalyst.

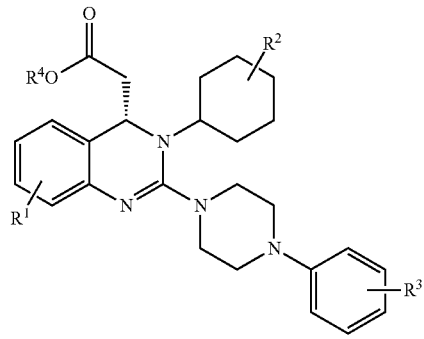

(I)

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claim 17 is cancelled.

Claims 1-16 were not reexamined.

\* \* \* \* \*